US011667700B2

(12) United States Patent
Porgador

(10) Patent No.: US 11,667,700 B2
(45) Date of Patent: Jun. 6, 2023

(54) ANTI-PCNA MONOCLONAL ANTIBODIES AND USE THEREOF

(71) Applicant: THE NATIONAL INSTITUTE FOR BIOTECHNOLOGY IN THE NEGEV LTD., Beer-Sheva (IL)

(72) Inventor: Ari-Angel Porgador, Lehavim (IL)

(73) Assignee: THE NATIONAL INSTITUTE FOR BIOTECHNOLOGY IN THE NEGEV LTD., Beer-Sheva (IL)

( * ) Notice: Subject to any disclaimer, the term of this patent is extended or adjusted under 35 U.S.C. 154(b) by 420 days.

(21) Appl. No.: 17/074,919

(22) Filed: Oct. 20, 2020

(65) Prior Publication Data

US 2021/0032320 A1 Feb. 4, 2021

Related U.S. Application Data

(63) Continuation of application No. 16/469,325, filed as application No. PCT/IL2017/051351 on Dec. 14, 2017, now Pat. No. 10,836,818.

(60) Provisional application No. 62/434,532, filed on Dec. 15, 2016.

(51) Int. Cl.
| | |
|---|---|
| *C07K 16/00* | (2006.01) |
| *A61K 39/395* | (2006.01) |
| *G01N 33/574* | (2006.01) |
| *C07K 16/18* | (2006.01) |
| *A61P 35/02* | (2006.01) |
| *A61K 39/00* | (2006.01) |

(52) U.S. Cl.
CPC .............. *C07K 16/18* (2013.01); *A61P 35/02* (2018.01); *G01N 33/57496* (2013.01); *A61K 2039/505* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2010/0240874 A1 | 9/2010 | Malkas et al. |
| 2015/0259407 A1 | 9/2015 | Hickey et al. |

FOREIGN PATENT DOCUMENTS

WO 2007098415 A2 8/2007

OTHER PUBLICATIONS

Mandelboim, O. (1996). Protection from lysis by natural killer cells of group 1 and 2 specificity is mediated by residue 80 in human histocompatibility leukocyte antigen C alleles and also occurs with empty major histocompatibility complex molecules. Journal of Experimental Medicine, 184(3), 913-922.
Lecoeur, H., (2001). A novel flow cytometric assay for quantitation and multiparametric characterization of cell-mediated cytotoxicity. Journal of Immunological Methods, 253(1-2), 177-187.
Rosental, B., et al., (2011). Proliferating Cell Nuclear Antigen is a Novel Inhibitory Ligand for the Natural Cytotoxicity Receptor NKp44. The Journal of Immunology, 187(11), 5693-5702.
Shemesh et al., Survival in acute myeloid leukemia is associated with NKp44 splice variants, Oncotarget, vol. 7, No. 22, 2016.
Shemesh et al., NKp44 and NKp30 splice variant profiles in decidua and tumor tissues: a comparative viewpoint, Oncotarget, Advance Publications 2016.
Pardoll, D. M. (2012). The blockade of immune checkpoints in cancer immunotherapy. Nature Reviews Cancer, 12(4), 252-264.
Horton, N. C. (2013). Novel Interaction between Proliferating Cell Nuclear Antigen and HLA I on the Surface of Tumor Cells Inhibits NK Cell Function through NKp44. PLoS ONE, 8(3), e59552.
International Search Report of PCT/IL2017/051351 Completed Feb. 27, 2018; dated Feb. 27, 2018, 2 pages.
Written Opinion of PCT/IL2017/051351 Completed Feb. 27, 2018; dated Feb. 27, 2018, 6 pages.
Paul, Fundamental Immunology, 3rd Edition, 1993, pp. 292-295.
Maccallum et al, J. Mol. Biol., 262, 732-745, 1996.
Vajdos et al., Journal of Molecular Biology, 2002, vol. 320, pp. 415-428.

*Primary Examiner* — Mark Halvorson
(74) *Attorney, Agent, or Firm* — The Roy Gross Law Firm, LLC; Roy Gross

(57) ABSTRACT

The present invention provides a monoclonal antibody or an antigen-binding portion thereof having increased binding affinity to cytoplasmic PCNA and blocks its interaction with NKp44. The present invention further provides use of the antibody or an antigen-binding portion thereof in the treatment of diseases associated with elevated expression of NKp44, such as cancer.

19 Claims, 27 Drawing Sheets
Specification includes a Sequence Listing.

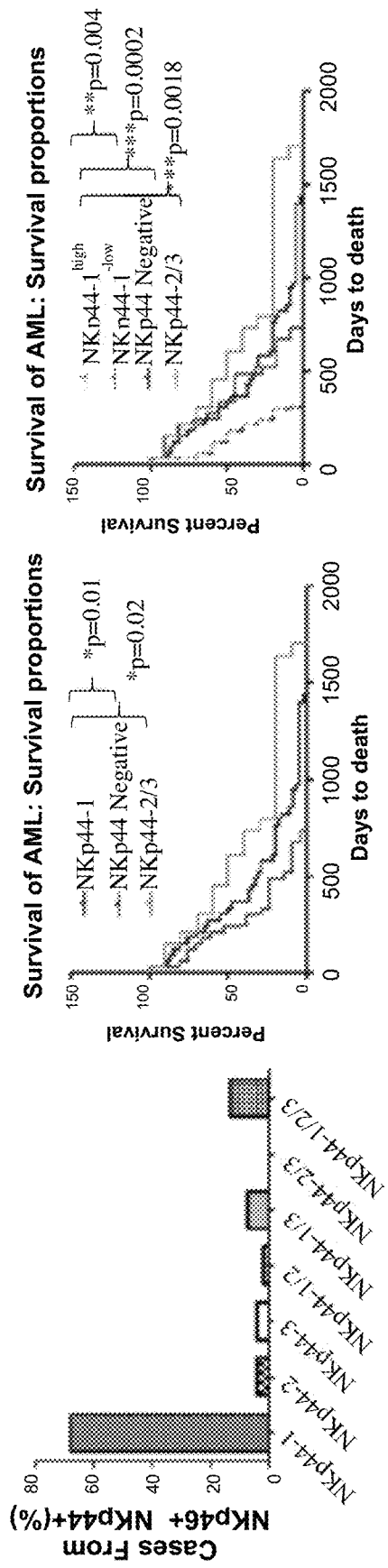

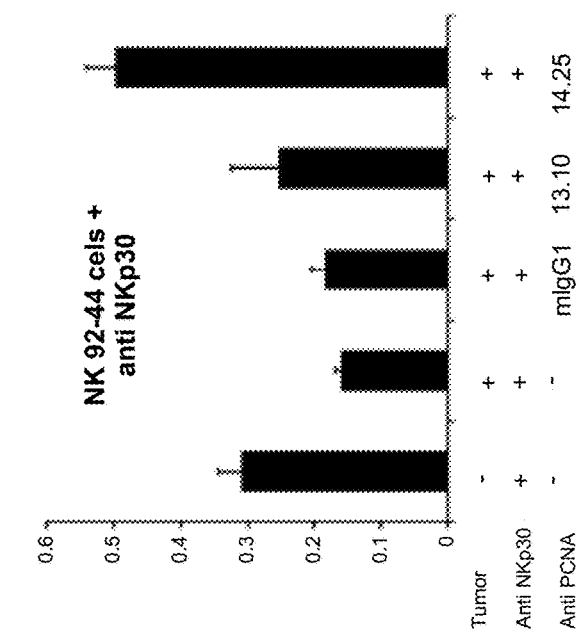
FIGURE 4C
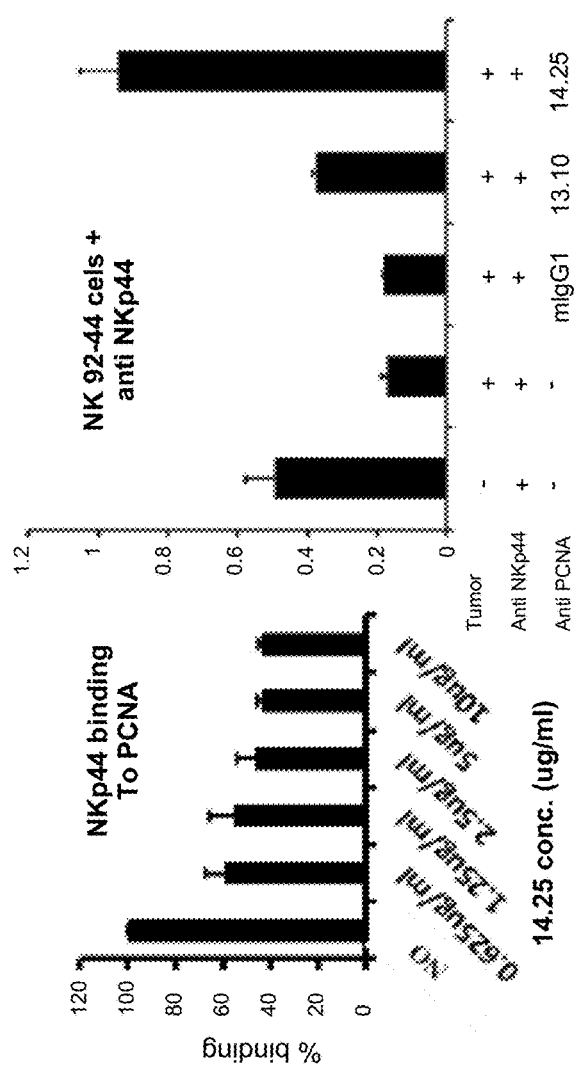
FIGURE 4B
FIGURE 4A

ANTI-PCNA MONOCLONAL ANTIBODIES AND USE THEREOF

CROSS-REFERENCE TO RELATED APPLICATIONS

This application is a continuation of U.S. application Ser. No. 16/469,325 filed Jun. 13, 2019, which is a National Phase of PCT Patent Application No. PCT/IL2017/051351 having International filing date of Dec. 14, 2017, which claims the benefit of priority of U.S. Provisional Patent Application No. 62/434,532 filed Dec. 15, 2016. The contents of above applications are all incorporated by reference as if fully set forth herein in their entirety.

FIELD OF INVENTION

The present invention is in the field of monoclonal antibodies.

BACKGROUND OF THE INVENTION

Alternative splicing of NKp44 RNA results in three splice variants which can be divided by the presence of an immunoreceptor tyrosine-based inhibition motif (ITIM) in the cytoplasmic portion of the receptor. NKp44-1 isoform has been shown to be ITIM positive, whereas NKp44-2 and -3 isoforms are ITIM negative. The ITIM mediates the inhibitory nature of the NKp44-PCNA (proliferating cell nuclear antigen) interaction.

There is a need for developing agents highly specific for the NKp44-1 to PCNA interaction, with the ability to block this interaction.

SUMMARY OF THE INVENTION

The present invention provides monoclonal antibodies or antigen-binding portions thereof having increased binding affinity to PCNA. Advantageously, the antibodies described herein are neutralizing antibodies. The present invention further provides compositions, kits and methods, such as for the use of the antibodies or antigen-binding portions thereof in the treatment of diseases associated with NKp44, specifically NKp44-1. The present invention further provides compositions, kits and methods, such as for the use of the antibodies or antigen-binding portions thereof in the detection and diagnosis of non-nuclear PCNA-associated diseases, such as cancer.

According to one aspect, the present invention provides an antibody or an antigen-binding portion thereof comprising three heavy chain CDRs (CDR-H) and three light chain CDRs (CDR-L), wherein:

CDR-H1 comprises the amino acid sequences selected from SEQ ID NO: 1 (GFSFNI) and SEQ ID NO: 21 (IYAMN),
CDR-H2 comprises the amino acid sequence as set forth in SEQ ID NO: 2 (RIRSKSNNYATY),
CDR-H3 comprises the amino acid sequence as set forth in SEQ ID NO: 3 (HPNYSGFNYPFAS),
CDR-L1 comprises the amino acid sequence as set forth in SEQ ID NO: 4 (RSSQSIVHSNGKTYFE),
CDR-L2 comprises the amino acid sequence as set forth in SEQ ID NO: 5 (KVSNRFS), and
CDR-L3 comprises the amino acid sequence as set forth in SEQ ID NO: 6 (FQGSHVPYT).

According to some embodiments, said CDR-H1 of the antibody or antigen-binding portion thereof comprises or consists of the amino acid sequence as set forth in SEQ ID NO: 22 (GFSFNIYAMN).

According to some embodiments, said CDR-H2 of the antibody or antigen-binding portion thereof comprises or consists of the amino acid sequence as set forth in SEQ ID NO: 23 (RIRSKSNNYATYYADSVKD).

According to some embodiments, said antibody or antigen-binding portion thereof comprises a variable region heavy chain comprising the amino acid sequence of SEQ ID NO: 7. According to some embodiments, said antibody or antigen-binding portion thereof comprises a constant region heavy chain comprising the amino acid sequence of SEQ ID NO: 9.

According to some embodiments, said antibody or antigen-binding portion thereof comprises a variable region light chain comprising the amino acid sequence of SEQ ID NO: 8. According to some embodiments, said antibody or antigen-binding portion thereof comprises a constant region light chain comprising the amino acid sequence of SEQ ID NO: 10.

According to another aspect, the present invention provides an antibody or an antigen-binding portion thereof comprising three heavy chain CDRs (CDR-H) and three light chain CDRs (CDR-L), wherein:

CDR-H1 comprises the amino acid sequences selected from SEQ ID NO: 11 (VYAFSS) or SEQ ID NO: 24 (SSWMN),
CDR-H2 comprises the amino acid sequence as set forth in SEQ ID NO: 12 (RIYPADGDTN),
CDR-H3 comprises the amino acid sequence as set forth in SEQ ID NO: 13 (WLRAMDY),
CDR-L1 comprises the amino acid sequence as set forth in SEQ ID NO: 14 (KASQNVGTNVA),
CDR-L2 comprises the amino acid sequence as set forth in SEQ ID NO: 15 (SASYRYS), and
CDR-L3 comprises the amino acid sequence as set forth in SEQ ID NO: 16 (QQYNSYPYT).

According to some embodiments, said CDR-H1 of the antibody or antigen-binding portion thereof comprises or consists of the amino acid sequence as set forth in SEQ ID NO: 25 (VYAFSSSWMN).

According to some embodiments, said CDR-H2 of the antibody or antigen-binding portion thereof comprises or consists of the amino acid sequence as set forth in SEQ ID NO: 26 (RIYPADGDTNYNGNFRG).

According to some embodiments, said antibody or antigen-binding portion thereof comprises a variable region heavy chain comprising the amino acid sequence of SEQ ID NO: 17. According to some embodiments, said antibody or antigen-binding portion thereof comprises a constant region heavy chain comprising the amino acid sequence of SEQ ID NO: 19.

According to some embodiments, said antibody or antigen-binding portion thereof comprises a variable region light chain comprising the amino acid sequence of SEQ ID NO: 18. According to some embodiments, said antibody or antigen-binding portion thereof comprises a constant region light chain comprising the amino acid sequence of SEQ ID NO: 20.

In one embodiment, the antibody or an antigen-binding portion thereof is selected from the group consisting of a Fv, Fab, F(ab') 2, scFV or a scFV$_2$ fragment.

In one embodiment, the antibody or antigen-binding portion thereof has increased binding affinity to PCNA. In one embodiment, the antibody or antigen-binding portion thereof has the ability to block the interaction between PCNA and NKp44-1.

According to another aspect, the present invention provides a pharmaceutical composition comprising the antibody, or an antigen-binding portion thereof, and a pharmaceutically acceptable carrier.

According to another aspect, the present invention provides a pharmaceutical composition comprising the antibody, or an antigen-binding portion thereof, and a pharmaceutically acceptable carrier, for use in treating an ITIM-associated disease, or an NKp44-1-associated disease or disorder, including but not limited to cancer.

According to another aspect, the present invention provides a method for treating a subject suffering from a ITIM-associated disease, including but not limited to cancer, the method comprising administering to said subject a pharmaceutical composition comprising a therapeutically effective amount of the antibody or an antigen-binding portion thereof of the present invention.

According to another aspect, the present invention provides a method for treating a subject suffering from a NKp44-1-associated disease, including but not limited to cancer, the method comprising administering to said subject a pharmaceutical composition comprising a therapeutically effective amount of the antibody or an antigen-binding portion thereof of the present invention.

In some embodiments, the method comprises the step of contacting the sample with an anti-membrane-associated PCNA antibody, and detecting binding of the antibody to membrane-associated PCNA. In some embodiments, increased levels of membrane-associated PCNA, is indicative of an NKp44-1-associated disease or severity thereof.

According to another aspect, the current invention provides a method of detecting non-nuclear PCNA (e.g., membrane-associated PCNA) in a subject, comprising detecting the levels of PCNA in a sample of a non-nuclear fraction derived from the subject, such as by contacting the non-nuclear fraction sample with an anti-PCNA antibody and detecting the binding between the non-nuclear PCNA and the antibody.

According to another aspect, the present invention provides method of diagnosing, prognosticating or determining the suitability for treatment of a subject afflicted with a NKp44-1-associated disease (e.g., cancer), comprising detecting whether PCNA is present in a sample derived from the subject, such as by contacting the sample with an anti-PCNA antibody and detecting binding between the non-nuclear PCNA and the antibody, wherein the presence of PCNA in the sample is indicative of a NKp44-1-associated disease in the subject.

In some embodiments, the sample comprises a non-nuclear fraction. In some embodiments, the anti-PCNA antibody has increased binding affinity to non-nuclear PCNA.

In some embodiments, the NKp44-1-associated disease is cancer. In some embodiments, the cancer is selected from: prostate cancer, leukemia, kidney cancer, head and neck cancer, tongue cancer, and breast cancer.

According to another aspect, the current invention provides a kit for detecting non-nuclear PCNA, comprising an antibody or antigen binding portion thereof.

Other features and advantages of the present invention will become apparent from the following detailed description.

BRIEF DESCRIPTION OF THE DRAWINGS

FIGS. 3A-3F. Poor survival of NKp44-1 profile in acute myelocytic leukemia (AML) patients. RNA-seq analysis of bone marrow samples obtained from AML patients (TCGA data): (A) Proportions of $NKp46^+NKp44^+$ (n=51) and $NKp46^+NKp44^-$ (n=115) patients from all $NKp46^+$ AML cases. (B) Survival of $NKp46^+NKp44^+$ (n=36) and $NKp46^+NKp44^-$ (n=60) patients having the "day of death" information recoded in the TCGA data; difference is not statistically significant. (C) Relative distribution of NKp44 splice variants in $NKp46^+NKp44^+$ (n=51) AML cases. (D) Percentages of NKp44 splice variant profiles from total $NKp46^+NKp44^+$ (n=51) AML cases. (E) Survival of $NKp46^+$ AML cases with a profile of NKp44-1 (n=24) vs. NKp44-2/3 (n=12) vs. $NKp44^-$ (n=60). (F) Survival of $NKp46^+$ AML cases with differential profile of NKp44-1: $NKp44-1^{high}$ (n=12) vs. $NKp44-1^{low}$ (n=12). NKp44-2/3 (n=12) vs. $NKp44^-$ (n=60) profiles (from E) are re-plotted for the ease of comparison.

FIGS. 4A-4C. Anti-PCNA mAbs block tumor-mediated suppression. mAbs were raised in our laboratory against PCNA. (A) Binding of recombinant NKp44 to plate-bound recombinant PCNA in the presence of titrated concentrations of mAb 14.25. Y-axis is % binding of NKp44 normalized to NKp44 binding w/o 14.25 (left column, 100%). IFNγ secretion by NK92-44 cells activated on plated bound anti-NKp44 (B) or anti NKp30 (C) in the presence of HeLa cells pre-coated with anti-PCNA antibodies or control mIgG1 as noted.

DETAILED DESCRIPTION OF THE INVENTION

Figure 1C:
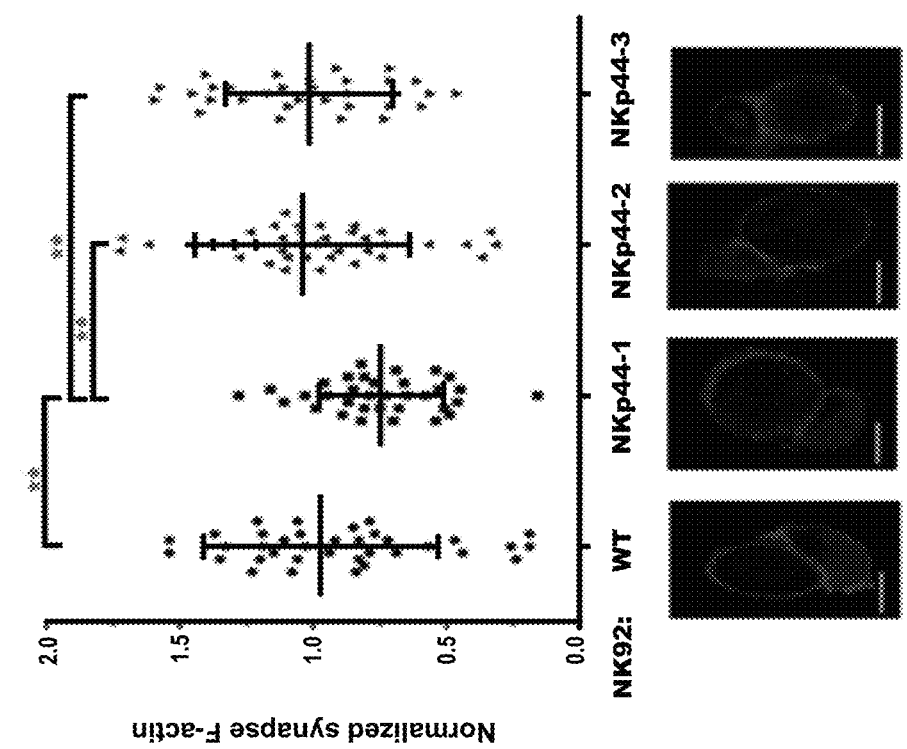
FIGS. 1A-1C. Over-expression of single NKp44 splice variant in NK92 cell line leads to a different function. NK92 cells were transduced with NKp44/NCR2 isoforms to over-express isoform 1, 2 and 3 (NK92-44-1, NK92-44-2, and NK92-44-3, respectively). (A) Relative IFNγ secretion by NK92-44-1, NK92-44-2, NK92-44-3 cell lines following 18 h incubation with HeLa GFP and HeLa GFP PCNA. (B) Example for relative quantification of immune synapse specific F-actin accumulation. Effector NK cells were co-incubated on confocal chamber slides with CFSE-labeled target HeLa cells, fixed and permeabilized, and stained with Phalloidin and DAPI. Representative image of NK effector-HeLa target interaction is shown (left panel); For image analysis (right panel), background fluorescence noise was eliminated using ImageJ mean threshold algorithm. In order to neglect florescent signal originated from target cell F-actin and variation in staining intensity; gated synapse F-actin MFI was divided by total conjugation MFI. (C) Analysis of synapse images of wildtype (wt) NK92, NK92-44-1, -2, and -3 cell lines co-incubated with CFSE-labeled target HeLa cells (n=30-40 images/group); images with over-saturated pixels were excluded from analysis. Representative images are below the histogram bars.

In some embodiments, the present invention is directed to an antibody or an antibody fragment thereof having increased binding affinity to PCNA, and the ability to block the interaction of PCNA and NKp44 isoform 1.

In some embodiments, the present invention is directed to an antibody or an antibody fragment thereof having increased binding affinity to PCNA, and the ability to block the interaction of PCNA and ITIM positive NKp44.

In some embodiment, NKp44 is isoform-1 NKp44 (or interchangeably "natural cytotoxicity triggering receptor 2" or "NCR2") having the polypeptide sequence as set forth in

SEQ ID NO: 35
(MAWRALHPLLLLLLLFPGSQAQSKAQVLQSVAGQTLTVRC

QYPPTGSLYEKKGWCKEASALVCIRLVTSSKPRTMAWTSRFTIWDDPDAG

FFTVTMTDLREEDSGHYWCRIYRPSDNSVSKSVRFYLVVSPASASTQTSW

TPRDLVSSQTQTQSCVPPTAGARQAPESPSTIPVPSQPQNSTLRPGPAAP

IALVPVFCGLLVAKSLVLSALLVWWGDIWWKTMMELRSLDTQKATCHLQQ

VTDLPWTSVSSPVEREILYHTVARTKISDDDDEHTL).

The present invention, in some embodiments, is directed to an isolated antibody or an isolated antibody fragment thereof having increased binding affinity to PCNA specifically, membrane-associated PCNA.

As used herein, the term "membrane-associated PCNA" refers to non-nuclear PCNA. In some embodiments, the methods, kits and compositions of the invention, provide anti-membrane-associated PCNA antibodies having no, or minimum affinity to nuclear PCNA.

In one embodiment, the antibody or antigen-binding portion thereof has the ability to block the interaction of PCNA and NKp44 isoform 1. In one embodiment, the antibody or antigen-binding portion thereof has minimal effect on the interaction between PCNA and any one of NKp44 isoform 2 and/or NKp44 isoform 3.

In one embodiment, the antibody or antigen-binding portion thereof substantially blocks NKp44-PCNA interaction.

In one embodiment, the antibody or antigen-binding portion thereof substantially enhances NK activity, such as following exposure to tumor cells.

The present invention is based in part on the finding of novel antibodies which block NKp44-PCNA interaction. As the antibodies disclosed herein have increased specificity to blocking interaction with NKp44 isoform 1 (i.e., ITIM positive), the disclosed antibodies or fragments thereof may be used for treating diseases associated with NKp44 ITIM+ (positive), such as cancer.

As described herein, the anti-PCNA antibodies of the invention can be used as a diagnostic and/or a prognosis agent for diseases or conditions wherein the NKp44 isoform 1 expression or activity is involved, such as cancer and specifically AML, as demonstrated herein.

An "anti-PCNA antibody", "an antibody which recognizes PCNA", or "an antibody against PCNA" is an antibody that binds to PCNA, with sufficient affinity and specificity. In some embodiments, an anti-PCNA antibody as disclosed herein has neutralizing activity over PCNA.

In some embodiments, antibody or antigen-binding portion thereof of the present invention, preferably binds to non-nuclear PCNA than to nuclear PCNA. As a non-limiting example, antibody or antigen-binding portion thereof of the present invention, as used herein "13-10-1" and "14-25-9" bind to non-nuclear PCNA with KD values of $8.99E^{-9}$ M and $3.54E^{-8}$ M, respectively.

As used herein, the terms "increased binding affinity" and "greater binding affinity" are interchangeable. In some embodiments, antibody or antigen-binding portion thereof of the present invention has a greater binding affinity to the non-nuclear PCNA compared to the nuclear PCNA. In one embodiment, greater affinity as used herein is by 10%. In one embodiment, greater affinity as used herein is by 30%. In one embodiment, greater affinity as used herein is by 50%. In one embodiment, greater affinity as used herein is by 75%. In one embodiment, greater affinity as used herein is by 100%. In one embodiment, greater affinity as used herein is by 150%. In one embodiment, greater affinity as used herein is by 250%. In one embodiment, greater affinity as used herein is by 500%. In one embodiment, greater affinity as used herein is by 1,000%. In one embodiment, greater affinity as used herein is by 1.5-fold. In one embodiment, greater affinity as used herein is by 2-fold. In one embodiment, greater affinity as used herein is by 5-fold. In one embodiment, greater affinity as used herein is by 10-fold. In one embodiment, greater affinity as used herein is by 50-fold. In one embodiment, greater affinity as used herein is by 100-fold. In one embodiment, greater affinity as used herein is by 500-fold. In one embodiment, greater affinity as used herein is by 1,000-fold.

The term "antibody" (also referred to as an "immunoglobulin") is used in the broadest sense and specifically encompasses monoclonal antibodies and antibody fragments so long as they exhibit the desired biological activity. In certain embodiments, the use of a chimeric antibody or a humanized antibody is also encompassed by the invention.

The basic unit of the naturally occurring antibody structure is a heterotetrameric glycoprotein complex of about 150,000 daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt.cines.fr/) (IMGT®/V-Quest) to identify variable region segments, including CDRs. See, e.g., Brochet, X. et al, Nucl. Acids Res. J6:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al, U.S. Dept. of Health and Human Services, "Sequence of Proteins of Immunological Interest" (1983).

TABLE 1

The amino acid sequences of the CDR sequences of the antibodies of the invention.

| mAb | mAb #1 (SEQ ID NO) | mAb #2 (SEQ ID NO) |
|---|---|---|
| CDR H1 (AbM) | GFSFNIYAMN (22) | VYAFSSSWMN (25) |
| CDR H1 (Chothia) | GFSFNI (1) | VYAFSS (11) |
| CDR H1 (Kabat) | IYAMN (21) | SSWMN (24) |
| CDR H2 (AbM and Chothia) | RIRSKSNNYATY (2) | RIYPADGDTN (12) |
| CDR H2 (Kabat) | RIRSKSNNYATYYADSVKD (23) | RIYPADGDTNYNGNFRG (26) |
| CDR H3 | HPNYSGFNYPFAS (3) | WLRANIDY (13) |
| CDR L1 | RSSQSIVHSNGKTYFE (4) | KASQNVGTNVA (14) |
| CDR L2 | KVSNRFS (5) | SASYRYS (15) |
| CDR L3 | FQGSHVPYT (6) | QQYNSYPYT (16) |

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA 57:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539). As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. In some cases, however, specific amino acid residues, for example in the framework regions, may be modified, so as to optimize performance of the humanized antibody. Importantly, the humanized antibody is expected to bind to the same antigen as the donor antibody that provides the CDRs. For further details, see e.g. U.S. Pat. No. 5,225,539 assigned to Medical Research Council, UK. The terms "a framework region from an acceptor human immunoglobulin" and "a framework region derived from an acceptor human immunoglobulin", and similar grammatical expressions are used interchangeably herein to refer to a framework region or portion thereof that has the same amino acid sequence of the acceptor human immunoglobulin.

As used herein, the terms "CAR-T cell" and "CAR-NK cell" refer to an engineered receptor which has specificity for at least one protein of interest (for example an immunogenic protein with increased expression following treatment with an epigenetic modifying agent) and is grafted onto an immune effector cell (a T cell or NK cell). In some embodiments, the CAR-T cell has the specificity of a monoclonal antibody grafted onto a T-cell. In some embodiments, the CAR-NK cell has the specificity of a monoclonal antibody grafted onto a NK-cell. In some embodiments, the T cell is selected from a cytotoxic T lymphocyte and a regulatory T cell.

CAR-T and CAR-NK cells and their vectors are well known in the art. Such cells target and are cytotoxic to the protein for which the receptor binds. In some embodiments, a CAR-T or CAR-NK cell targets at least one viral protein. In some embodiments, a CAR-T or CAR-NK cell targets a plurality of viral proteins. In some embodiments, a CAR-T or CAR-NK cell targets a viral protein with increased expression due to contact with an epigenetic modifying agent.

Construction of CAR-T cells is well known in the art. In one non-limiting example, a monoclonal antibody to a viral protein can be made and then a vector coding for the antibody will be constructed. The vector will also comprise a costimulatory signal region. In some embodiments, the costimulatory signal region comprises the intracellular domain of a known T cell or NK cell stimulatory molecule. In some embodiments, the intracellular domain is selected from at least one of the following: CD3Z, CD27, CD28, 4-1BB, OX40, CD30, CD40, PD-1, ICOS, lymphocyte function-associated antigen-1 (LFA-1), CD2, CD 7, LIGHT, NKG2C, B7-H3, and a ligand that specifically binds with CD83. In some embodiments, the vector also comprises a CD3Z signaling domain. This vector is then transfected, for example by lentiviral infection, into a T-cell.

As used herein, the term "immunotherapeutic agent" refers to any molecule, compound, solution or cell that elicits an active immune response. In some embodiments, the immunotherapeutic agent activates the immune system. In some embodiments, the immunotherapeutic agent is a cancer-targeting immunotherapeutic agent. In some embodiments, the immunotherapeutic agent elicits an active immune response against a cancer or cell thereof. In some embodiments, the immunotherapeutic agent elicits a general immune response. In some embodiments, the immunotherapeutic agent elicits an immune response against a specific protein, group of proteins, transcript or group of transcripts. Each possibility represents a separate embodiment of the invention. An immune checkpoint inhibitor would be a non-limiting example of an immunotherapeutic agent that elicits a general immune response. A chimeric antigen receptor CAR-T cell, CAR-NK cell or a cytotoxic monoclonal antibody would be non-limiting examples of immunotherapeutic agents that elicit a response against a specific protein. A vaccine would be a non-limiting example of an immunotherapeutic agent that elicit a response against a group of proteins or transcripts (or even a singular protein or transcript). In some embodiments, the immunotherapeutic agent is selected from: a CAR-T cell, a vaccine, an antibody and an immune checkpoint inhibitor. In some embodiments, the immunotherapeutic agent is a CAR-T cell, a vaccine, a cytotoxic antibody or an immune checkpoint inhibitor. Each possibility represents a separate embodiment of the invention.

In some embodiments, the immunotherapeutic agent binds to the immunogenic protein. In some embodiments, the immunotherapeutic agent binds to the increased immunogenic protein. In such embodiments, the immunotherapeutic agent is an agent that targets a specific protein or proteins. In such embodiments, the immunotherapeutic agent is selected from a CAR-T cell, a CAR-NK cell, a vaccine, and a cytotoxic monoclonal antibody. In some embodiments, the virus is an endogenous virus and the immunotherapeutic agent directly binds to the increased immunogenic protein.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed antibodies to be used in accordance with the methods provided herein may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies as described herein are neutralizing antibodies. "Neutralization", as discussed here, is defined as the reduction of NKp44-PCNA interaction by antibodies of the invention.

In some embodiments, neutralizing antibodies include: antibodies, fragments of antibodies, Fab and F(ab')2, single-domain antigen-binding recombinant fragments and natural nanobodies.

In some embodiments, the present invention provides nucleic acid sequences encoding the antibody of the present invention.

In one embodiment, an antibody as described herein comprises a light chain variable domain encoded by a DNA sequence comprising the following nucleic acid sequence (SEQ ID NO: 27):
TGACATTGTGATGACTCAGTCTCAAAAAATCATGTCCACATCAGTAGGAG

ACAGGGTCAGCGTCACCTGCAAGGCCAGTCAGAATGTGGGTACTAATGTA

GCCTGGTATCAACAGAAACCAGGGCAATCTCCTAAAGTACTGATTTACTC

GGCATCCTACCGGTACAGTGGAGTCCCTGATCGCTTCACAGGCAGTGGAT

CTGGGACAGATTTCACTCTCAGCATCAGCAATGTGCAGTCTGAAGACTTG

GCAGAGTATTTCTGTCAGCAATATAACAGCTATCCGTACACGTTCGGAGG

GGGGACCAAGCTGGAAATAAAA.

In one embodiment, an antibody as described herein comprises a light chain constant domain encoded by a DNA sequence comprising the following nucleic acid sequence (SEQ ID NO: 28):
CGGGCTGATGCTGCACCAACTGTATCCATCTTCCCACCATCCAGTGAGCA

GTTAACATCTGGAGGTGCCTCAGTCGTGTGCTTCTTGAACAACTTCTACC

CCAAAGACATCAATGTCAAGTGGAAGATTGATGGCAGTGAACGACAAAAT

```
GGCGTCCTGAACAGTTGGACTGATCAGGACAGCAAAGACAGCACCTACAG

CATGAGCAGCACCCTCACGTTGACCAAGGACGAGTATGAACGACATAACA

GCTATACCTGTGAGGCCACTCACAAGACATCAACTTCACCCATTGTCAAG

AGCTTCAACAGGAATGAGTGTTAGA.
```

In one embodiment, an antibody as described herein comprises a heavy chain variable domain encoded by a DNA sequence comprising the following nucleic acid sequence

```
(SEQ ID NO: 29):
GAGCCTGGGGCCTCAGTGAAGATTTCCTGCAAGGCTTCTGTCTACGCATT

CAGTAGTTCCTGGATGAACTGGGTGAAGCAGAGGCCTGGAAAGGGTCTTG

AGTGGATTGGACGGATTTATCCTGCAGATGGAGATACTAACTACAATGGG

AACTTCAGGGGCAAGGCCACACTGACTGCAGACAAATCCTCCAGCACAGC

CTACATGCAACTCAGCAGTCTGACATCTGAGGACTCTGCGGTCTACTTCT

GTGCAAGATGGTTACGGGCTATGGACTACTGGGGTCAAGGAACCTCAGTC

ACCGTCTCCTCA.
```

In one embodiment, an antibody as described herein comprises a heavy chain constant domain encoded by a DNA sequence comprising the following nucleic acid sequence

```
(SEQ ID NO: 30):
GCCAAAACAACATACCCCCCATCTGTCTATCCACTGGCCCCTGGATCTGC

TGCCCAAACTAACTCCATGGTGACCCTGGGATGCCTGGTCAAGGGCTATT

TCCCTGAGCCAGTGACAGTGACCTGGAACTCTGGATCCCTGTCCAGCGGT

GTGCACACCTTCCCAGCTGTCCTGCAGTCTGACCTCTACACTCTGAGCAG

CTCAGTGACTGTCCCCTCCAGCACCTGGCCCAGCGAGACCGTCACCTGCA

ACGTTGCCCACCCGGCCAGCAGCACCAAGGTGGACAAGAAAATTGTGCCC

AGGGATTGTGGTTGTAAGCCTTGCATATGTACAGTCCCAGAAGTATCATC

TGTCTTCATCTTCCCCCCAAAGCCCAAGGATGTGCTCACCATTACTCTGA

CTCCTAAGGTCACGTGTGTTGTGGTAGACATCAGCAAGGATGATCCCGAG

GTCCAGTTCAGCTGGTTTGTAGATGATGTGGAGGTGCACACAGCTCAGAC

GCAACCCCGGGAGGAGCAGTTCAACAGCACTTTCCGCTCAGTCAGTGAAC

TTCCCATCATGCACCAGGACTGGCTCAATGGCAAGGAGTTCAAATGCAGG

GTCAACAGTGCAGCTTTCCCTGCCCCCATCGAGAAAACCATCTCCAAAAC

CAAAGGCAGACCGAAGGCTCCACAGGTGTACACCATTCCACCTCCCAAGG

AGCAGATGGCCAAGGATAAAGTCAGTCTGACCTGCATGATAACAGACTTC

TTCCCTGAAGACATTACTGTGGAGTGGCAGTGGAATGGGCAGCCAGCGGA

GAACTACAAGAACACTCAGCCCATCATGGACACAGATGGCTCTTACTTCG

TCTACAGCAAGCTCAATGTGCAGAAGAGCAACTGGGAGGCAGGAAATACT

TTCACCTGCTCTGTGTTACATGAGGGCCTGCACAACCACCATACTGAGAA

GAGCCTCTCCCACTCTCCTGGTAAATGA.
```

In one embodiment, an antibody as described herein comprises a light chain variable domain encoded by a DNA sequence comprising the following nucleic acid sequence

```
(SEQ ID NO: 31):
TGATGTTGTGATGACCCAAACTCCGCTCTCCCTGCCTGTCAGTCTTGGAG

ATCAAGCCTCCATCTCTTGCAGATCTAGTCAGAGCATTGTACATAGTAAT

GGAAAGACCTATTTTGAATGGTACCTTCAGAAACCAGGCCAGTCTCCAAA

GCTCCTGATCTACAAAGTTTCCAACCGATTTTCTGGGGTCCCAGACAGGT

TCAGTGGCAGTGGATCAGGGACAGAATTCACACTCAAGATCAGCAGAGTG

GAGGCTGAGGATCTGGGAGTTTATTACTGCTTTCAAGGTTCACATGTTCC

GTACACGTTCGGAGGGGGGACCAAGCTGGAAATAAAA.
```

In one embodiment, an antibody as described herein comprises a light chain constant domain encoded by a DNA sequence comprising the following nucleic acid sequence

```
(SEQ ID NO: 32):
CGGGCTGATGCTGCACCAACTGTATCCATCTTCCCACCATCCAGTGAGCA

GTTAACATCTGGAGGTGCCTCAGTCGTGTGCTTCTTGAACAACTTCTACC

CCAAAGACATCAATGTCAAGTGGAAGATTGATGGCAGTGAACGACAAAAT

GGCGTCCTGAACAGTTGGACTGATCAGGACAGCAAAGACAGCACCTACAG

CATGAGCAGCACCCTCACGTTGACCAAGGACGAGTATGAACGACATAACA

GCTATACCTGTGAGGCCACTCACAAGACATCAACTTCACCCATTGTCAAG

AGCTTCAACAGGAATGAGTGTTAG.
```

In one embodiment, an antibody as described herein comprises a heavy chain variable domain encoded by a DNA sequence comprising the following nucleic acid sequence

```
(SEQ ID NO: 33):
AAGCTGGTGGAGTCTGGTGGAGGATTGGTGCAGCCTACAGGGTCATTGAA

ACTCTCATGTGTAACCTCTGGATTCAGTTTCAATATCTACGCCATGAACT

GGGTCCGCCAGGCTCCAGGAAAGGGTTTGGAATGGGTTGCTCGCATAAGA

AGTAAAAGTAATAATTATGCAACATATTATGCCGATTCAGTGAAAGACAG

ATTCACCATCTCCAGAGATGATTCAGAAAGCATGCTCTATCTCCAAATGA

ACAACTTGAAAACTGAGGACACAGCCATGTATTACTGTATGAGACACCCC

AATTACTCCGGCTTTAACTACCCGTTTGCTTCCTGGGGCCCAGGGACTCT

GGTCACTGTCTCTGCA.
```

In one embodiment, an antibody as described herein comprises a heavy chain constant domain encoded by a DNA sequence comprising the following nucleic acid sequence

```
(SEQ ID NO: 34):
GCCAAAACGACACCCCCATCTGTCTATCCACTGGCCCCTGGATCTGCTGC

CCAAACTAACTCCATGGTGACCCTGGGATGCCTGGTCAAGGGCTATTTCC

CTGAGCCAGTGACAGTGACCTGGAACTCTGGATCCCTGTCCAGCGGTGTG

CACACCTTCCCAGCTGTCCTGCAGTCTGACCTCTACACTCTGAGCAGCTC
```

-continued

```
AGTGACTGTCCCCTCCAGCACCTGGCCCAGCCAGACCGTCACCTGCAACG

TTGCCCACCCGGCCAGCAGCACCAAGGTGGACAAGAAAATTGTGCCCAGG

GATTGTGGTTGTAAGCCTTGCATATGTACAGTCCCAGAAGTATCATCTGT

CTTCATCTTCCCCCCAAAGCCCAAGGATGTGCTCACCATTACTCTGACTC

CTAAGGTCACGTGTGTTGTGGTAGACATCAGCAAGGATGATCCCGAGGTC

CAGTTCAGCTGGTTTGTAGATGATGTGGAGGTGCACACAGCTCAGACGAA

ACCCCGGGAGGAGCAGATCAACAGCACTTTCCGTTCAGTCAGTGAACTTC

CCATCATGCACCAGGACTGGCTCAATGGCAAGGAGTTCAAATGCAGGGTC

AACAGTGCAGCTTTCCCTGCCCCCATCGAGAAAACCATCTCCAAAACCAA

AGGCAGACCGAAGGCTCCACAGGTGTACACCATTCCACCTCCCAAGGAGC

AGATGGCCAAGGATAAAGTCAGTCTGACCTGCATGATAACAAACTTCTTC

CCTGAAGACATTACTGTGGAGTGGCAGTGGAATGGGCAGCCAGCGGAGAA

CTACAAGAACACTCAGCCCATCATGGACACAGATGGCTCTTACTTCGTCT

ACAGCAAGCTCAATGTGCAGAAGAGCAACTGGGAGGCAGGAAATACTTTC

ACCTGCTCTGTGTTACATGAGGGCCTGCACAACCACCATACTGAAGAG

CCTCTCCCACTCTCCTGGTAAATGA.
```

In one embodiment, an antibody as described herein is encoded by a DNA molecule comprising a DNA sequence having at least 75% identity to a DNA sequence as described herein. In one embodiment, an antibody as described herein is encoded by a DNA molecule comprising a DNA sequence having at least 80% identity to a DNA sequence as described herein. In one embodiment, an antibody as described herein is encoded by a DNA molecule comprising a DNA sequence having at least 85% identity to a DNA sequence as described herein. In one embodiment, an antibody as described herein is encoded by a DNA molecule comprising a DNA sequence having at least 90% identity to a DNA sequence as described herein. In one embodiment, an antibody as described herein is encoded by a DNA molecule comprising a DNA sequence having at least 95% identity to a DNA sequence as described herein.

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding a polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

Methods for Treatment and Diagnosis

As used herein the term "treatment" refers to clinical intervention in an attempt to alter the course of disease in the individual being treated, and can be performed either for prophylaxis or during the course of clinical pathology. Desirable effects of treatment include preventing occurrence or recurrence of the disease, alleviation of symptoms, reducing a pathological consequence of the disease, reducing the rate of disease progression, amelioration of the disease state, remission or improved prognosis. The term "treatment" may also encompass ex vivo procedures affecting cells or tissues in culture.

As used herein the term "subject" refers to an individual, or a patient, which is a vertebrate, e.g., a mammal, including especially a human.

As defined herein, binding of an antigen molecule by an antibody results in blocking said antigen's activity. The term "blocking" used herein is interchangeable with "attenuating", "inhibiting", "reducing" and "decreasing".

In some embodiments of the methods described herein, blocking is reducing by more than 2%. In some embodiments of the methods described herein, blocking is reducing by more than 5%. In some embodiments of the methods described herein, blocking is reducing by more than 10%. In some embodiments of the methods described herein, blocking is reducing by more than 25%. In some embodiments of the methods described herein, blocking is reducing by more than 50%. In some embodiments of the methods described herein, blocking is reducing by more than 75%. In some embodiments of the methods described herein, blocking is reducing by more than 90%. In some embodiments of the methods described herein, blocking is reducing by more than 95%. In some embodiments of the methods described herein, blocking is reducing by 99%.

As defined herein "biological sample" refers to a physical specimen from any animal. In another embodiment, biological sample is obtained from a mammal. In another embodiment, biological sample is obtained from a human. In another embodiment, biological sample is obtained well within the capabilities of those skilled in the art. The biological sample includes, but not limited to, biological fluids such as serum, plasma, vitreous fluid, lymph fluid, synovial fluid, follicular fluid, seminal fluid, amniotic fluid, milk, whole blood, urine, cerebrospinal fluid, saliva, sputum, tears, perspiration, mucus, and tissue culture media, including tissue extracts such as homogenized tissue, and cellular extracts. In another embodiment, a biological sample is a biopsy. In another embodiment, a biological sample is a resected tumor. In another embodiment, a biological sample includes histological sections processed as known by one skilled in the art. The terms sample and biological sample used herein, are interchangeable.

As defined herein, non-nuclear fraction refers to any tissue or cell extract excluding the cellular nucleus. In one embodiment, non-nuclear extract includes the cytoplasm. In one embodiment, non-nuclear extract includes cellular organelles. In one embodiment, non-nuclear extract includes the mitochondrion, endoplasmic reticulum, Golgi apparatus, lysosome, exosome and others. In one embodiment, non-nuclear extract includes cellular membrane or fragments thereof. In one embodiment, non-nuclear extract includes proteins. In one embodiment, non-nuclear proteins include cytoplasm and peripheral proteins. In one embodiment, non-nuclear extract includes soluble molecules. In one embodiment, non-nuclear extract includes membrane-associated molecules. In one embodiment, membrane associated molecules are integral, spanning or in proximity to the cellular membrane.

In some embodiments, to create a non-nuclear profile of molecules, cellular compartments, or organelles are homogenized in standard ways known for those skilled in the art. In some embodiments, different fractionation procedures are used to enrich the fractions of molecules. In one embodiment, the molecules obtained are passed over several fractionation columns. In one embodiment, the fractionation columns employ a variety of detectors used in tandem or parallel to generate the molecule profile for the organ, cell, cellular compartment, or organelle.

As used herein the term "disease" refers to any condition which would benefit from treatment with the antibody.

In one embodiment, the present invention concerns a method for treating, diagnosing, prognosticating or determining the suitability for treatment of a subject suffering from cancer, specifically AML.

As used herein, "cancer" or "pre-malignancy" are diseases associated with cell proliferation. Non-limiting types of cancer include carcinoma, sarcoma, lymphoma, leukemia, blastoma and germ cells tumors. In one embodiment, carcinoma refers to tumors derived from epithelial cells including but not limited to breast cancer, prostate cancer, lung cancer, pancreas cancer, and colon cancer. In one embodiment, sarcoma refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to Hodgkin lymphoma, non-Hodgkin lymphoma, multiple myeloma and immunoproliferative diseases. In one embodiment, leukemia refers to tumors derived from hematopoietic cells that leave the bone marrow and tend to mature in the blood including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme. In one embodiment, germ cell tumors refer to tumors derived from germ cells including but not limited to germinomatous or seminomatous germ cell tumors (GGCT, SGCT) and nongerminomatous or nonseminomatous germ cell tumors (NGGCT, NSGCT). In one embodiment, germinomatous or seminomatous tumors include but not limited to germinoma, dysgerminoma and seminoma. In one embodiment, non-germinomatous or non-seminomatous tumors refers to pure and mixed germ cells tumors including but not limited to embryonal carcinoma, endodermal sinus tumor, choriocarcinoma, tearoom, polyembryoma, gonadoblastoma and teratocarcinoma.

In some embodiments, monoclonal antibodies of the present invention are useful for the diagnosis, detection, staging, and therapy of a disease. In some embodiments, monoclonal antibodies of the present invention are useful for the diagnosis, detection, staging, and therapy of a human disease. In some embodiments, monoclonal antibodies of the present invention are useful for the diagnosis, detection, staging, and therapy of cancer.

In one embodiment, the monoclonal antibodies and fragments thereof of the present invention are humanized or fully human.

In some embodiment, the present invention provides a method of diagnosing or treating a malignancy in a subject comprising administering to the subject a therapeutically effective amount of a therapeutic conjugate comprising the monoclonal antibodies of the present invention or fragment thereof or an antibody fusion protein or fragment thereof, wherein the monoclonal antibodies of the present invention or fragment thereof or antibody fusion protein or fragment thereof is bound to at least one diagnostic and/or therapeutic agent and then formulated in a pharmaceutically suitable excipient.

The use of monoclonal antibodies for in-vitro diagnosis is well-known to one skilled in the art. For example, see Carlsson et al., Bio/Technology 7 (6): 567 (1989). For example, monoclonal antibodies can be used to detect the presence of a tumor-associated antigen in tissue from biopsy samples. Monoclonal antibodies also can be used to measure the amount of tumor-associated antigen in clinical fluid samples using techniques such as radioimmunoassay, enzyme-linked immunosorbent assay, and fluorescence immunoassay. Conjugates of tumor-targeted monoclonal antibodies and toxins can be used to selectively kill cancer cells in vivo (Spalding, Bio/Technology 9(8): 701 (1991); Goldenberg, Scientific American Science & Medicine 1(1): 64 (1994)). For example, therapeutic studies in experimental animal models have demonstrated the anti-tumor activity of antibodies carrying cytotoxic radionuclides.

Also described herein is a cancer cell targeting diagnostic or therapeutic conjugate comprising an antibody component that comprises a monoclonal antibody or fragment thereof of any of the antibodies of the present invention, or an antibody fusion protein or fragment thereof, wherein the antibody component is bound to at least one diagnostic or at least one therapeutic agent. In one embodiment, the diagnostic conjugate is a photoactive diagnostic/detection agent. In one embodiment, the diagnostic conjugate is an ultrasound detectable agent. In one embodiment, the diagnostic conjugate is an MRI contrast agent. In another embodiment, the diagnostic/detection agent is a radionuclide with an energy between 20 and 4,000 keV.

Furthermore, the present invention includes methods of diagnosing cancer in a subject. In some embodiments, diagnosis is accomplished by administering a diagnostically effective amount of a diagnostic conjugate, formulated in a pharmaceutically suitable excipient, and detecting said label. The monoclonal antibodies of the present invention or derived fusion proteins or fragments thereof may be conjugated to the diagnostic/detection agent or be administered unconjugated to the diagnostic/detection agent, but before, concurrently, or after administration of the diagnostic/detection agent. In one embodiment, a suitable non-radioactive diagnostic/detection agent is a contrast agent suitable for magnetic resonance imaging (MRI), X-rays, computed tomography (CT) or ultrasound. In another embodiment, magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

In some embodiments, contrast agents, such as MRI contrast agents, contemplated in the present invention include, but not limited to, gadolinium ions, lanthanum ions, dysprosium ions, iron ions, manganese ions or other comparable label, CT contrast agents, and ultrasound contrast agents. In another embodiment, paramagnetic ions are suitable for the present invention. In one embodiment, paramagnetic ions include chromium$^{3+}$, manganese$^{2+}$, iron$^{3+}$, iron$^{2+}$, cobalt$^{2+}$, nickel$^{2+}$, copper$^{2+}$, neodymium$^{3+}$, samarium$^{3+}$, ytterbium$^{3+}$, gadolinium$^{3+}$, vanadium$^{2+}$, terbium$^{3+}$, dysprosium$^{3+}$, holmium$^{3+}$ and erbium$^{3+}$, with gadolinium being particularly preferred. In another embodiment, ions useful in other contexts, such as X-ray imaging, include but are not limited to lanthanum$^{3+}$, gold$^{3+}$, lead$^{2+}$, and especially bismuth$^{3+}$. In another embodiment, metals are also useful in diagnostic/detection agents, including those for magnetic resonance imaging techniques. In one embodiment, these metals include, but are not limited to: Gadolinium, manganese, iron, chromium, copper, cobalt, nickel, dysprosium, rhenium, europium, terbium, holmium and neodymium. In another embodiment, loading an antibody component with radioactive metals or paramagnetic ions may require reacting the antibody with a reagent having a long tail to which are attached a multiplicity of chelating groups for binding the ions. In one embodiment, such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

In some embodiments, conjugated diagnostic agents are radiopaque and contrast materials. In one embodiment these radiopaque diagnostic agents are used for enhancing X-rays and computed tomography, and include iodine compounds, barium compounds, gallium compounds, thallium compounds, etc. In another embodiment, specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

In some embodiments, the conjugated diagnostic agent is a fluorescent agent. In another embodiment, fluorescent labeling compounds include fluorescein isothiocyanate, rhodamine, phycoerytherin, renographin, phycocyanin, allophycocyanin, o-phthaldehyde and fluorescamine. In one embodiment, rhodamine and fluorescein are often linked via an isothiocyanate intermediate. In one embodiment, fluorescently-labeled antibodies are particularly used for flow cytometry analysis.

In some embodiments, the antibodies, fusion proteins, and fragments thereof of this invention can be detectably labeled by coupling the antibody to a chemiluminescent compound. In one embodiment, chemiluminescent labeling compounds include, but are not limited to, luminol, isoluminol, an aromatic acridinium ester, an imidazole, an acridinium salt and an oxalate ester, and others.

In some embodiments, a bioluminescent compound can be used to label the antibodies and fragments thereof the present invention. In one embodiment, bioluminescent labeling compounds include, but are not limited to luciferin, luciferase and aequorin.

According to another aspect, the present invention provides a method of treatment of a subject suffering from a disease, the method comprises administering to said subject a therapeutically effective amount of at least one antibody, fusion protein and fragments thereof of the invention directed against NKp44 isoform 1, or any fragment thereof.

The term "a therapeutically effective amount" refers to an amount effective, at dosages and for periods of time necessary, to achieve the desired therapeutic or prophylactic result. The exact dosage form and regimen would be determined by the physician according to the patient's condition.

Pharmaceutical Compositions

The present invention also contemplates pharmaceutical formulations for human medical use, which comprise as the active agent at least one antibody which recognizes PCNA, for the manufacture of a therapeutic composition for the treatment, diagnosis or prophylaxis of the conditions variously described herein.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician.

Although an appropriate dosage of a molecule (an antibody or a fragment thereof) of the invention varies depending on the administration route, type of molecule (polypeptide, polynucleotide, organic molecule etc.) age, body weight, sex, or conditions of the patient, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Suitable dosing regimens of combination chemotherapies are known in the art and described in, for example, Saltz et al. Proc ASCO 1999, 18, 233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

According to another aspect, the invention provides a pharmaceutical composition comprising as an active ingredient a therapeutically effective amount of the polypeptide of the present invention, and pharmaceutically acceptable carrier and/or diluents. In some embodiments, the pharmaceutical composition facilitates administration of a compound to an organism.

In another embodiment, the pharmaceutical compositions of the invention may be formulated in the form of a pharmaceutically acceptable salt of the polypeptides of the present invention or their analogs, or derivatives thereof. In another embodiment, pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned. The carrier may comprise, in total, from about 0.1% to about 99.99999% by weight of the pharmaceutical compositions presented herein.

As used herein, the term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the polypeptide of the invention, preferably in a substantially purified form, together with a suitable amount of carrier so as to provide the form for proper administration to the subject.

According to an embodiment of the invention, pharmaceutical compositions contain 0.1%-95% of the polypeptide(s) of the present invention, derivatives, or analogs thereof. According to another embodiment of the invention, pharmaceutical compositions contain 1%-70% of the polypeptide(s) derivatives, or analogs thereof. According to another embodiment of the invention, the composition or formulation to be administered may contain a quantity of polypeptide(s), derivatives, or analogs thereof, according to embodiments of the invention in an amount effective to treat the condition or disease of the subject being treated.

An embodiment of the invention relates to polypeptides of the present invention, derivatives, or analogs thereof, presented in unit dosage form and prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

According to one embodiment, the compositions of the present invention are administered in the form of a pharmaceutical composition comprising at least one of the active components of this invention (the chimeric polypeptides) together with a pharmaceutically acceptable carrier or diluent. In another embodiment, the compositions of this invention can be administered either individually or together in any conventional oral, parenteral or transdermal dosage form. In some embodiments, the pharmaceutical composition further comprises at least one anticancer agent such as a chemotherapeutic agent. In some embodiments, the pharmaceutical composition is adopted for combined administration with an anticancer therapy such as chemotherapy, radiotherapy, immunotherapy, hormonal therapy, toxin therapy or surgery.

As used herein, the terms "administering," "administration," and like terms refer to any method which, in sound medical practice, delivers a composition containing an active agent to a subject in such a manner as to provide a therapeutic effect.

Depending on the location of the tissue of interest, the polypeptide of the present invention can be administered in any manner suitable for the provision of the polypeptides to cells within the tissue of interest. Thus, for example, a composition containing the polypeptides of the present invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In some embodiments, the pharmaceutical compositions comprising the chimeric polypeptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

According to some embodiments, the chimeric polypeptides of the present invention, derivatives, or analogs thereof can be delivered in a controlled release system. In another embodiment, an infusion pump can be used to administer the peptide such as the one that is used, for example, for delivering insulin or chemotherapy to specific organs or tumors. In another embodiment, the peptides of the invention are administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

The presently described peptides, derivatives, or analogs thereof may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, it will be appreciated that the peptides of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is affected or diminution of the disease state is achieved.

In some embodiments, the peptides are administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the polypeptide is the amount of the polypeptide necessary for the in vivo measurable expected biological effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

Pharmaceutical compositions containing the presently described polypeptide as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

In one embodiment, compositions including the preparation of the present invention formulated in a compatible pharmaceutical carrier are prepared, placed in an appropriate container, and labeled for treatment of an indicated condition.

In one embodiment, compositions of the present invention are presented in a pack or dispenser device, such as an FDA approved kit, which contains, one or more unit dosages forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); "Monoclonal Antibodies: Methods and Protocols". Vincent Ossipow, Nicolas Fischer. Humana Press (2014); "Monoclonal Antibodies: Methods and Protocols". Maher Albitar. Springer Science & Business Media (2007), all of which are incorporated by reference. Other general references are provided throughout this document.

Materials and Methods

Recombinant Human PCNA Production

The pET-28 or pMAL-c2x vectors were used to produce recombinant human PCNA (hPCNA) in Rosetta™ 2 (DE3) cells. Plasmids containing the mRNA sequence of PCNA were transformed into Rosetta™ 2 cells via heat shock and grown on LB+Kan+CP agar plates. A fresh colony of transformed bacteria was grown overnight in a 5 ml of LB+Kan+CP in an incubator shaker set to 37° C. and at 250 rpm. The next day, bacteria calls were diluted 1:100 into a 500 ml of LB+Kan+CP (to discard dead cells) and grown to an O.D. of 0.6-0.8 ($\lambda$=650 nm). Isopropyl β-D-1-thiogalactopyranoside (IPTG) was added for the induction of the PCNA (0.5 mM) and cells were further incubated for 4 h at 26° C. (hPCNA). Cells were then centrifuged, and the pellet was resuspended with solution A (20 mM Tris-HCl pH 8.0, 0.5 M NaCl, 20 mM Imidazole), sonicated six times (20 seconds with 40 seconds intervals) and sieved through 0.45 μm (Sartorius Stedimbiotech) filter before loaded on a His-tag or Amyloseresin beads. Purification of His-tagged proteins was done using a Gravity-flow Column with "HisPur™ Ni-NTA Resin" Bead kit (Thermo-Scientific; Binding Capacity ≤60 mg of a 28 kDa 6× His-tagged protein from a bacterial source per milliliter of settled resin) according to kit's protocol. Purification of MBP-tagged proteins was done using the Amylose resin beads (Catalog #E8035S).

Kinetic Analysis of the Antibody by Surface Plasmon Resonance

A ProteOn™ XPR36 Protein Interaction Array System (Bio-Rad) was used to measure the affinity of the monoclonal antibody 14-25-9 to his-tagged recombinant PCNA. For the assay, a HTG chip and ProteOn Manager Version 3.1.0.6 (Bio-Rad Laboratories) was employed. After activation of the chip using EDC/S-NHS amine coupling procedure the ligand immobilization process was performed with histagged recombinant PCNA and His-tagged IL-2 as a control at a flow rate of 30 μl/min in different flow cells. Different analyte (14-25-9) concentrations (100-0 nM) were injected at a flow rate of 40 μl/min, each followed by regeneration of the surface using 50 mM NaOH. Data were analyzed using the Bivalent binding model.

Cell Lines and Cell Culture

The following cell lines were used: A549, human lung adenocarcinoma (American Type Culture Collection CCL-185); HeLa, human cervical adenocarcinoma (ATCC CCL-2); MDA-MB-435, human melanoma (https://www.atcc.org/Products/All/HTB-129.aspx) (ATCC HTB-129); K562, human chronic myelogenous leukemia (ATCC CCL-243) and 721.221cw6, stable 721.221 (WIC class I-negative human B cell line) transfectants expressing HLA-C molecules as generated previously (J Exp Med. 1996 Sep. 1; 184(3):913-22). Cells were cultured in either DMEM or RPMI-1640 (Gibco, Life Technologies) medium supplemented with 10% FBS and 1% penicillin/streptomycin. Human NK cell leukemia derived NK-92 cell line (ATCC CRL-2407) was retrovirally transduced with the FLAG-tagged NKp44 constructs to produce NK-92-NKp44 cell line. Retroviral transduction was performed as previously described. Stable NK-92-NKp44 cell line was then cultured in alpha-MEM medium (Gibco, Life Technologies) supplemented with 10% horse serum, 10% FBS, 0.2 mM myo-inositol (Sigma), 0.1 mM β-mercaptoethanol (Sigma), 20 μM folic acid (Fisher Scientific), 100 IU/ml of recombinant human IL-2 (PeproTech), and 1% penicillin/streptomycin (Life Technologies).

Isolation and Culture of Primary Human NK Cells

With prior approval from the Ben-Gurion University of the Negev Institutional Review Board, human primary natural killer cell isolation was done from peripheral blood of healthy volunteer donors with their informed consent, using the RosetteSep Human NK cell Enrichment Cocktail kit (Stem Cell Technologies). After purification, cells were cultured in CellGro stem cell serum-free growth medium (CellGenix) supplemented with 10% heat-inactivated human plasma from healthy donors, 1 mM sodium pyruvate, 2 mM L-glutamine, 1×MEM non-essential amino acids, 1% penicillin/streptomycin, 10 mM HEPES (Life Technologies), and 300 IU/ml human IL-2 (PeproTech).

ELISA for IFN-γ Secretion Assay

A paired set of purified and biotinylated anti-human IFN-γ antibody (BioLegend) was used for the sandwich ELISA of IFN-γ secretion assay. 96-well U-bottom plates (NUNC) were pre-coated with either 0.5 μg/ml Anti-human NKp30 mAb (R&D Systems) diluted in $Na_2HPO_4$ buffer (0.1 M, pH 9) or only buffer for 18 h at 4° C. Tumor cells were incubated either with 1×PBS, anti-mouse IgG1 or different conc. of 14-25-9 mAb (2, 5 and 10 μg/ml in studies using primary NK cells and 10, 20 and 30 μg/ml while NK-92-NKp44 cell line). Then they were co-cultured (Effector:Target ratio 1:3) with either primary human NK cells or NK-92-NKp44 in the previously coated 96-well U-bottom plates for 18 h in a 37° C., 5% $CO_2$ incubator. Post incubation, the supernatant from each well was transferred to corresponding wells in 96-well flat-bottom ELISA plates coated previously with 0.25 μg/ml purified anti-human IFN-γ, incubated and recaptured using 0.25 m/ml biotinylated anti-human IFN-γ. Captured IFN-γ was quantitated using HRP-tagged streptavidin (Jackson ImmunoResearch) and TMB substrate (Dako) in a multi-plate ELISA reader.

Flow Cytometry Based NK Cell-Mediated Lysis Assay

As in the IFN-γ secretion assay, carboxyfluorescein diacetate succinimidyl ester-stained (CellTrace™ CFSE Cell Proliferation Kit, Thermo) tumor cells were incubated initially either with 1×PBS, anti-mouse IgG1 or different conc. of 14-25-9 mAb and then co-cultured with primed primary human NK cells or NK-92-NKp44 cells in 96-well U-bottom plates pre-coated with either 0.5 m/ml anti-human NKp30 mAb or buffer for 4 h (37° C., 5% $CO_2$). Assay analysis was based on following gating strategy: CFSE-positive tumor cells were subjected to Live/Dead discrimination (PI negative or positive staining in accordance). The percentage of specific cytotoxicity was calculated as follows (Journal of Immunological Methods 2001 253:177-187):

$$\% \text{ Specific Lysis} = \frac{100 \times (\% \text{ Sample Lysis} - \% \text{ Basal Lysis})}{100 - \% \text{ Basal Lysis}}$$

Example 1

NKp44-1 has a Unique Role as an Immune Checkpoint

Previous reports have shown that tumor-expressed PCNA can be utilized by cancer cells to suppress NK activity, through interaction with the NK receptor NCR2/NKp44. To assess the role of each NKp44 splice variant, NK92 cells were transfected with cDNA encoding for each of the three NKp44 splice variants. qPCR analysis of the splice variants profile of the three NK92 transfectants, (i.e., NK92-44-1, NK92-44-2 and NK92-44-3) showed dominant expression of the transfected splice variant in all three.

Figure 1A:
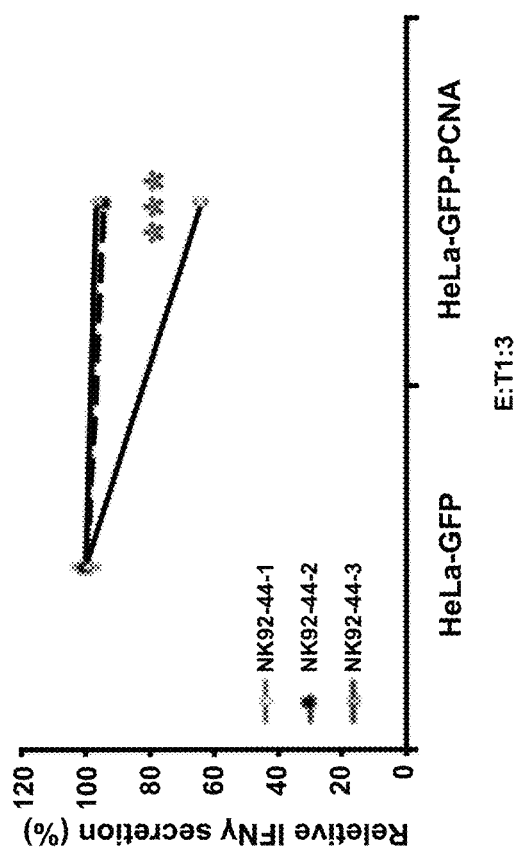
Figure 1B:
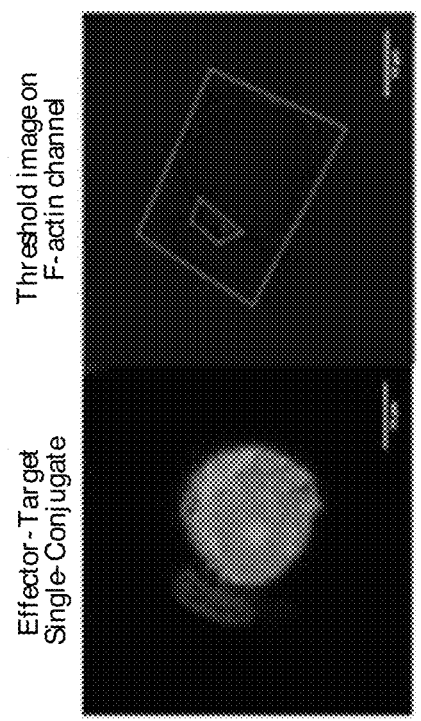

Over-expression of PCNA by co-cultured (target) cells inhibited IFNγ secretion by NK92-44-1 cells, but not by NK92-44-2 and NK92-44-3 cells (FIG. 1A). The inventors next explored whether PCNA-impaired and PCNA-responsive NK functional phenotypes can influence the cytoskeleton rearrangement that is necessary for the formation of stable lytic immune synapses. Stable lytic immune synapse formation was examined in each NKp44 splice variant-transfected NK92 cell lines. NK92 wt (parental), NK92-44-1, NK92-44-2 and NK92-44-3 (effector) cells were co-incubated with HeLa cells expressing CFP alone or CFP-PCNA fusion protein and the relative accumulation of F-actin at the immune synapse was assessed (FIG. 1B, C). It was surprisingly found that overexpression of the NKp44-1 splice variant resulted in a significant reduction (−22.6%±3.9%) in the relative amount of F-actin accumulating at the immune synapse in interactions of NK92-44-1 cells with PCNA overexpressing target cells (FIG. 1C). In contrast, splice variant 2 and 3-transfected NK92 cells showed no significant decrease in F-actin accumulation (+6.9% and +4.6%, respectively) as compared to the control WT NK92 effector cells (FIG. 1C.)

Figure 2A:
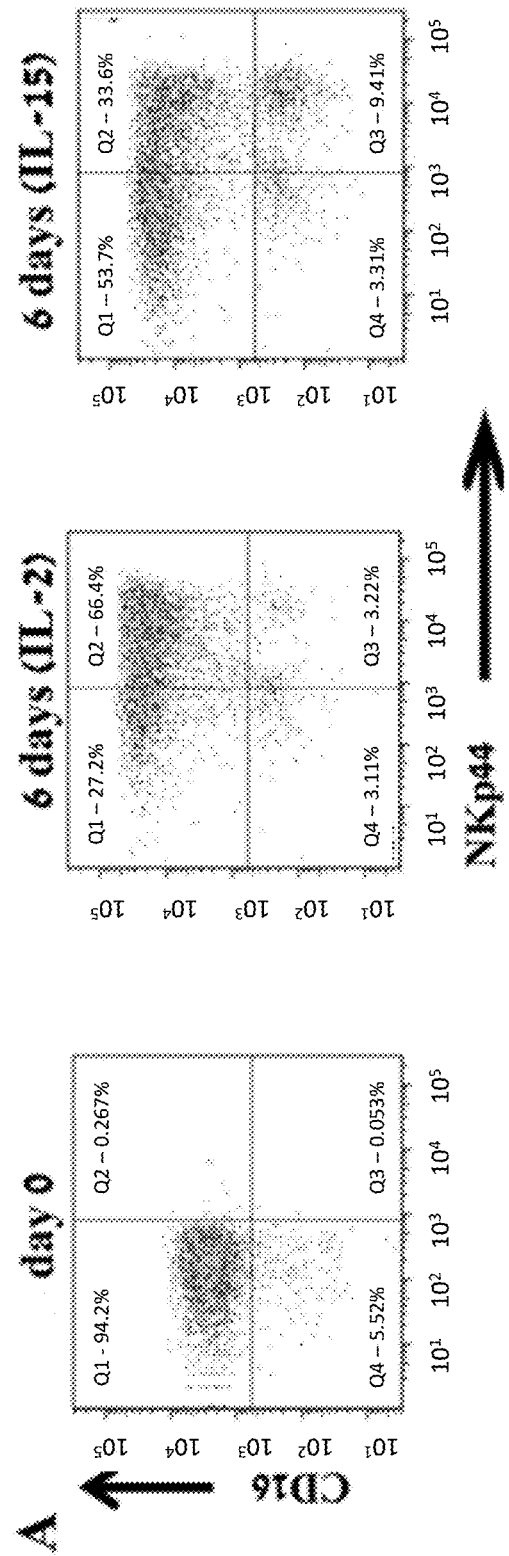
FIGS. 2A-2D. Expression of NKp44 splice variants and function of primary peripheral NK cells following culture with IL-2 or with IL-15. Primary human NK cells were isolated from blood and cultured for 6 days in the presence of IL-2 or IL-15. (A) Flow-cytometry based analysis of CD16 and NKp44 expression at day 0 and day 6 for $CD3^-/CD56^+$ gated cells. (B) qPCR analysis of NKp44 splice variants expression in primary NK cells at day 0 and following 6 days of treatment with IL-2 or with IL-15. Function of 6 days IL-2 (C)- or IL-15 (D)-cultured primary human NK cells; lysis of HeLa GFP PCNA cells compared to lysis of HeLa GFP cells with or w/o blocking with anti NKp44 (p44-8 mAb). Bars, ±SD. *, $p<0.05$; , $p<0.01$; *, $p<0.001$; Unpaired t-test, two-tail.
Figure 2B:
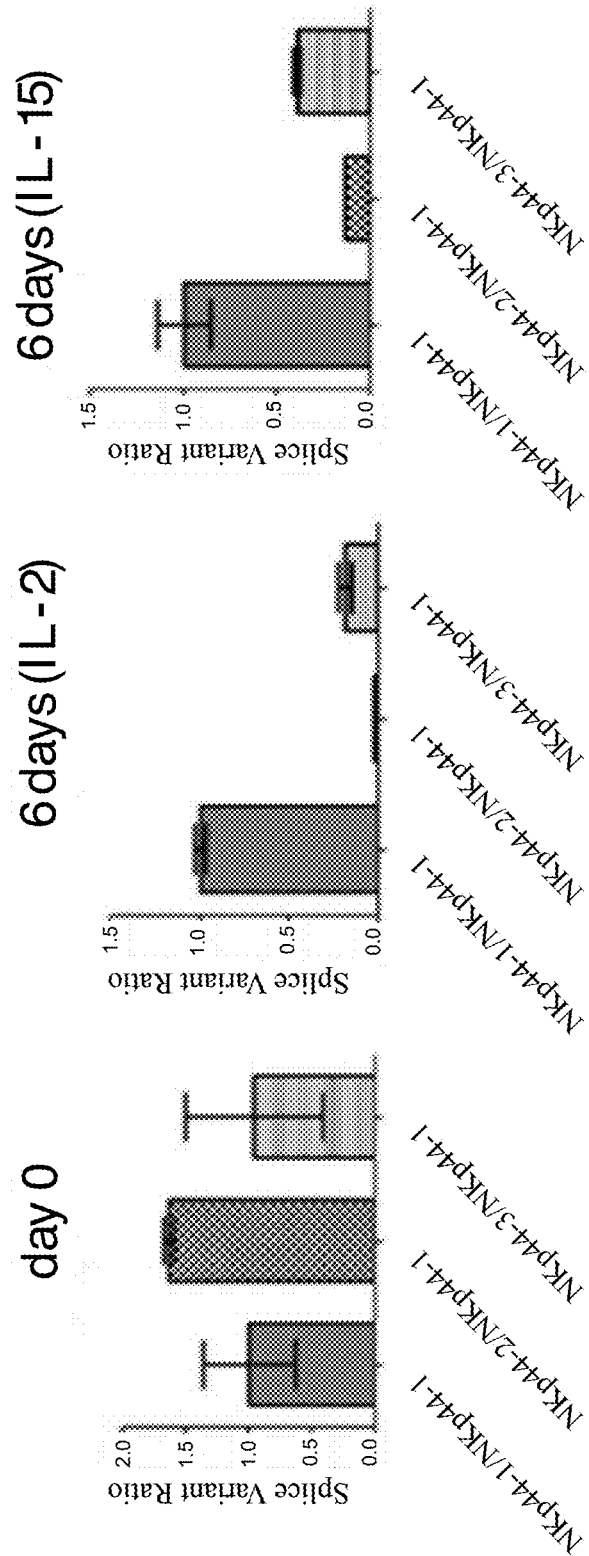

To further test this finding in primary NK cells, human NK cells were isolated from peripheral blood mononuclear cells (PBMCs) and cultured in the presence of IL-2 or IL-15 for 6 days. Indeed, NKp44 was not detected on the surface of resting CD3−/CD56+/CD16+ and CD3−/CD56+/CD16− primary NK cells by flow cytometry, but was up regulated in the presence of IL-2 or IL-15 (FIG. 2A). qPCR analysis of total NKp44 mRNA revealed similar results to NKp44 protein surface expression. When differential expression of NKp44 splice variants was further examined by qPCR, NKp44-1 and NKp44-3 were both significantly up-regulated, while NKp44-2 expression remained low. However, the NKp44-1 splice variant was more highly upregulated as compared to NKp44-3 (FIG. 2B).

Figure 2D:
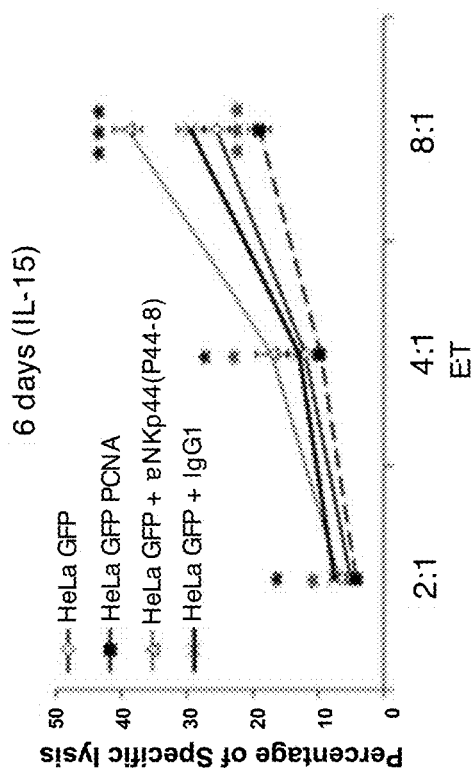
Figure 2C:
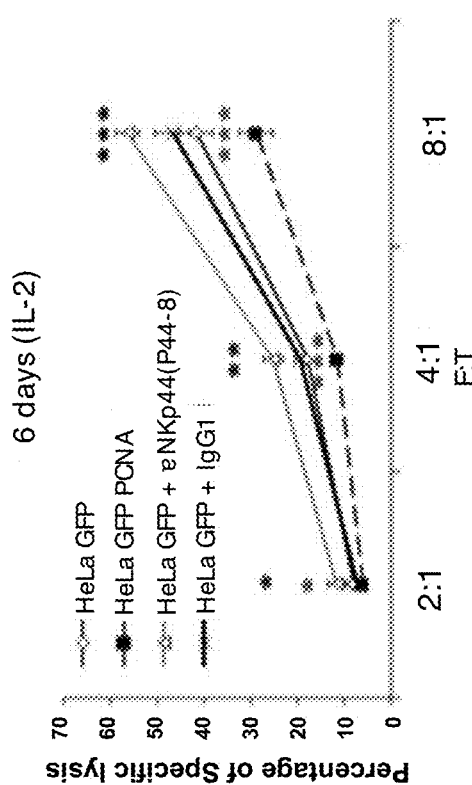

In a PCNA overexpression system model, IL-2 activated primary NK cells exhibited lower lytic activity towards PCNA-overexpressing HeLa target cells as compared to control HeLa cells (FIG. 2C, HeLa GFP vs. HeLa GFP PCNA). The same functional outcome was observed also for IL-15 cultured primary NK cells (FIG. 2D, HeLa GFP vs. HeLa GFP PCNA). Both phenomena correlate with the dominance of NKp44-1 splice variant expression after culturing primary NK with IL-2 or IL-15 (FIG. 2B). These findings indicate that the impaired functional phenotype of primary NK cells that results in suppressed lysis of cancer target cells, may be associated with NKp44-1 dominant expression.

Example 1 shows that high expression of NKp44-1 is associated with an impaired functional phenotype of peripheral NK cells, indicating NKp44-1's role as an immune checkpoint.

Example 2

Poor Survival of NKp44-1 Profile in Acute Myelocytic Leukemia (AML)

Figures 3A, 3B, 3C:
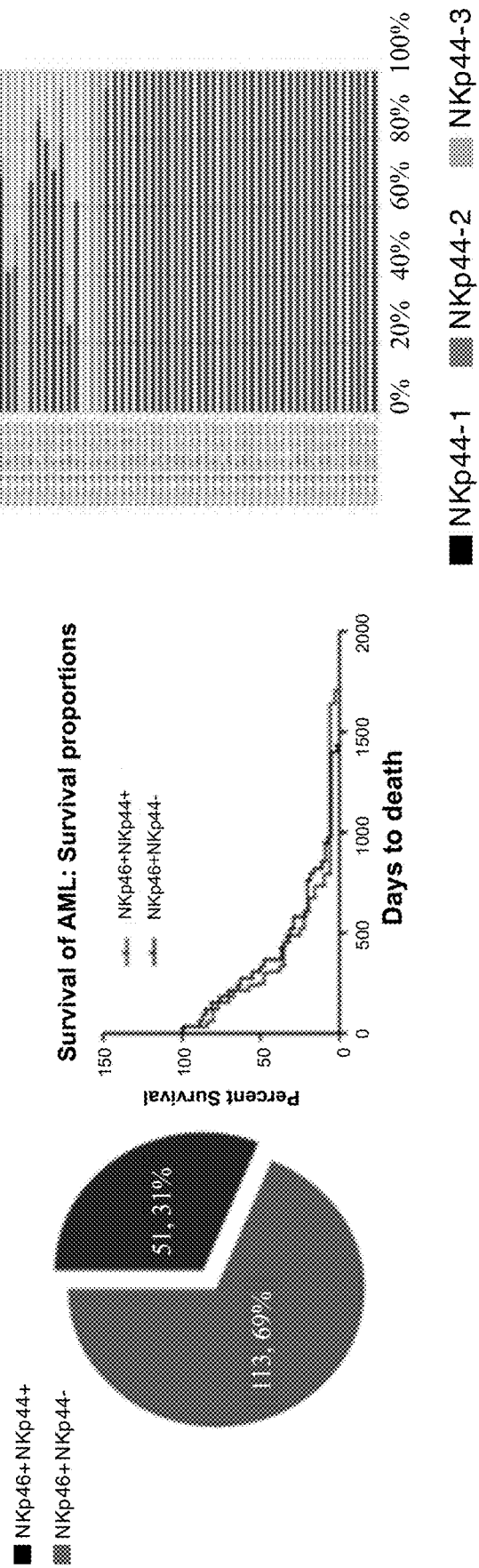

To further explore the physiological role of NKp44-1 in a cancerous state, a retrospective analysis on RNA-seq data obtained from peripheral blood samples of AML, patients deposited in the Cancer Genome Atlas (TCGA) was performed. 173 peripheral blood samples that had RNA-seq data were analyzed by first filtering the peripheral blood samples for the presence of NK cells using expression of the NK cell-specific receptor, NKp46 (i.e. total NKp46). 164 out of 173 cases were NKp46 positive and were chosen for further analysis. From the 164 NKp46 positive cases, 31% were NKp44 positive (i.e. total NKp44; FIG. 3A).

Thereafter, the contribution of NKp44 expression to the survival of AML patients was examined by comparing NKp46+NKp44+ and NKp46+NKp44− groups. Only 60 cases of NKp46+NKp44− and 36 cases of NKp46+NKp44+ had the "days to death" data deposited in the TCGA. No difference was seen in the percent survival between the NKp46+NKp44+ and NKp46+NKp44− cases groups (FIG. 3B).

To further investigate the role of NKp44 in AML associated morbidity, the expression of NKp44 isoforms was analyzed as NCR2 mRNA can be spliced into three different splice variants: NKp44-1, -2 and -3.

The relative RNAseq-based expression of the NKp44 splice variants in the NKp46+NKp44+ samples is detailed in FIG. 3C. Individual AML patients manifested a broad spectrum of NKp44 splice variants expression, ranging from a single NKp44 splice variant expressed to a mixed splice variant expression profile. Nearly two thirds of the NKp46+ NKp44+ cases expressed only the NKp44-1 splice variant (FIG. 3D). Thus, NKp46+NKp44-1+-only were considered as samples having a NKp44-1 profile, whereas the NKp44-2/3 profile was defined to include all other NKp46+ samples, whether they expressed NKp44-2 or NKp44-3 alone, or with expression of NKp44-1. NKp46+NKp44− samples were defined as having a NKp44 negative profile.

FIG. 3E shows that the survival of the NKp44-1 profile group was significantly lower than the NKp44-negative and the NKp44-2/3 profile groups. To better characterize the association between NKp44-1 expression levels and survival of AML patients, the NKp44-1 profile was further divided into NKp44-1 high (top half of expression) and NKp44-1 low (bottom half of expression) profiles. The inventors then plotted percent survival of AML cases for NKp44-1high, NKp44-1low, NKp44-2/3 and NKp44 negative profiles. The percent survival of NKp44-1low, NKp44-

2/3 and NKp44 negative profiles did not differ significantly. However, the patient group bearing the NKp44-1high profile manifested a significantly lower survival rate (FIG. 3F).

Example 2 shows that an NKp44-1 profile indicates poor survival of patients diagnosed with AML.

Example 3

Manipulation of NCR2-Based Immune Checkpoint with Anti-PCNA mAbs

Anti-PCNA mAbs capable of inhibiting NKp44/NCR2 binding to PCNA were generated in attempt to block the NCR2-isoform 1-based immune checkpoint. Mice were immunized with recombinant PCNA, splenocytes fused to myeloma counterpart and then screened for colonies positive for binding to PCNA and for inhibiting binding of NKp44 to PCNA.

Only two clones were able to block NKp44-PCNA interaction: 13.10 (30% blocking) and 14.25 (55% blocking, FIG. 4A). Blocking efficacy directly correlated with the ability of these mAbs to enhance NK function following exposure to tumor cells (FIG. 4B, C). Note that NK cells were either pre-activated with anti-NKp44 (that does not block NKp44-PCNA interaction) or with anti-NKp30. In both cases, addition of several cancer cell lines (e.g. HeLa) in 1:2 ET ratio inhibited NK function. Addition of these anti-PCNA mAbs enhanced NK function to a level higher than the primary stimulation (FIG. 4B, C). This indicates that target cancer cells come with inhibitory activating signals and if the inhibitory signal (e.g. PCNA) is blocked, then the NK activating signal mediated by the cancer cell contribute to NK function.

Example 4

Sequencing the Light and Heavy Chains of the Anti-PCNA mAbs

Figure 5B:
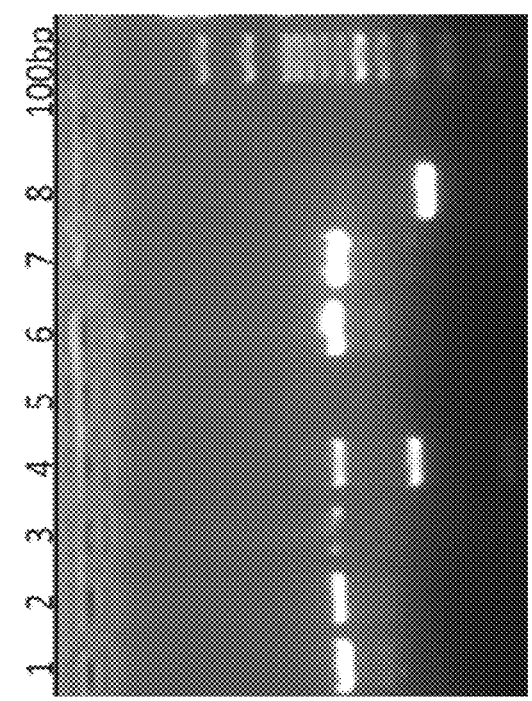
FIGS. 5A-5B depict light chain agarose gel electrophoresis under the procedures for generating the mAbs described herein. Each lane shows PCR product of the light chain amplified with each one of the 8 forward degenerate primers and the reverse primer (lanes 1-8).
Figure 5A:
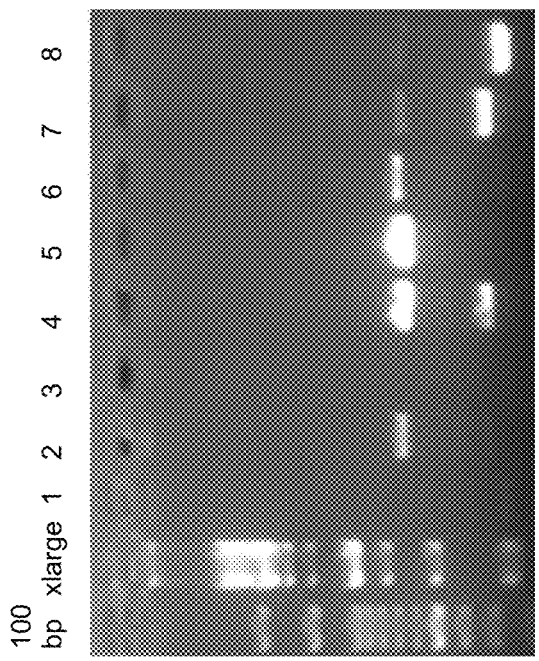

RNA was extracted from the hybridoma cell pellet using TRI Reagent (Sigma Cat. T9424, Lot. BCBQ3717V). Following visualizing of the extracted RNA integrity by agarose-gel electrophoresis, the RNA was used for cDNA preparation using SuperScript First-Strand Synthesis System (Invitrogen Cat. 11904-018, Lot. 1404272) with random primers and oligodT. The heavy chain was amplified from the coding region by PCR reaction using primers that targeted the constant and variable region separately. The light chain was amplified from the coding region by PCR reactions using degenerated-forward primers target the N-terminal sequence of the variable region and reverse primer that targets the respective constant region (FIGS. 5A-B). PCR products were visualized by agarose-gel electrophoresis, and the corresponding bands were extracted from the gel and taken for sequencing analysis. Sequencing was performed on ABI3730xl genetic analyzer according to SOP 11-001 using BigDye V1.1 chemistry and sequencing files were generated (AB1 and SEQ). When no bands were obtained by PCR reaction, new primers were designed to amplify the relevant regions of the heavy and light chains and sequenced as described above. DNA sequences of the heavy and light chains were analyzed to yield the respective protein sequences using IMGT database and/or ExPASy tool.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Example 5

Production of Specific Monoclonal Antibody Against Membranal PCNA

Figure 6A:
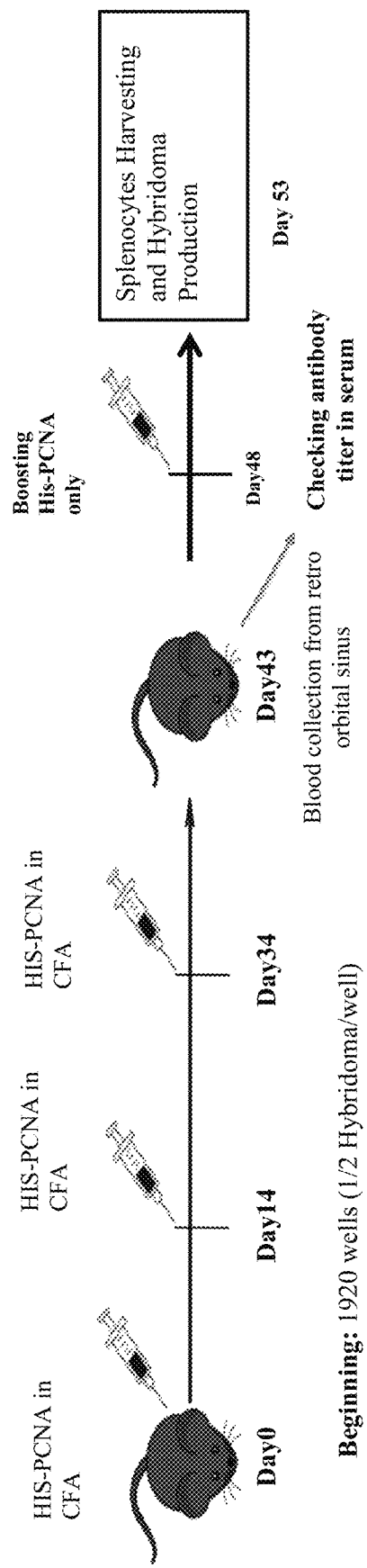
FIGS. 6A-6C. (A) Schematic representation of immunization schedule in mice for hybridoma production (B) Screening strategies for selection of specific monoclonal antibody producing clone. (C) ELISA result representing inhibition of NKp44 receptor binding to MBP-PCNA by cell culture soup of selected clones as well as membrane PCNA staining by FACS.
Figure 6C:
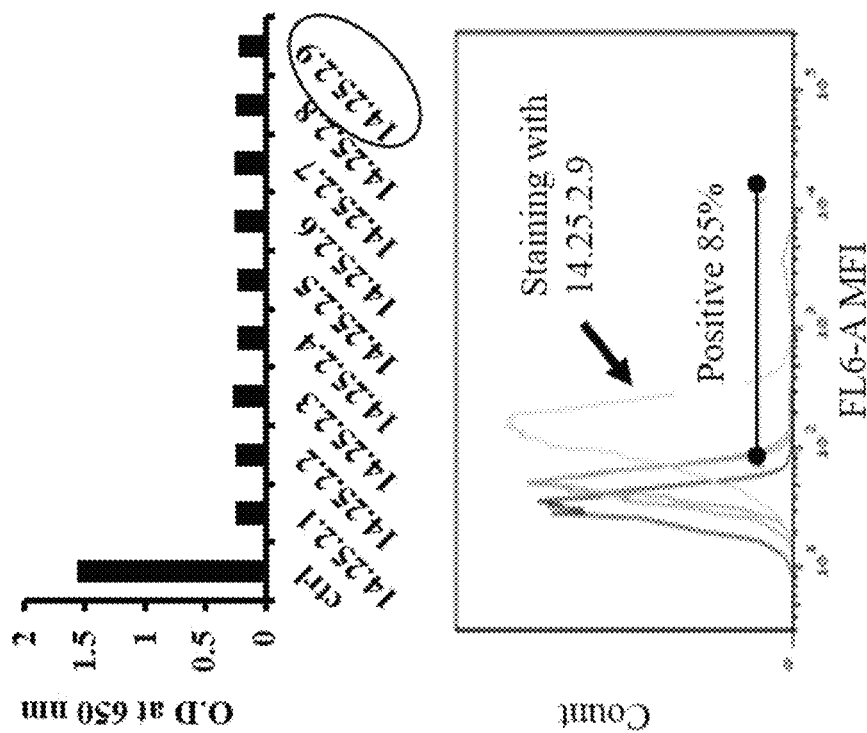
Figure 6B:
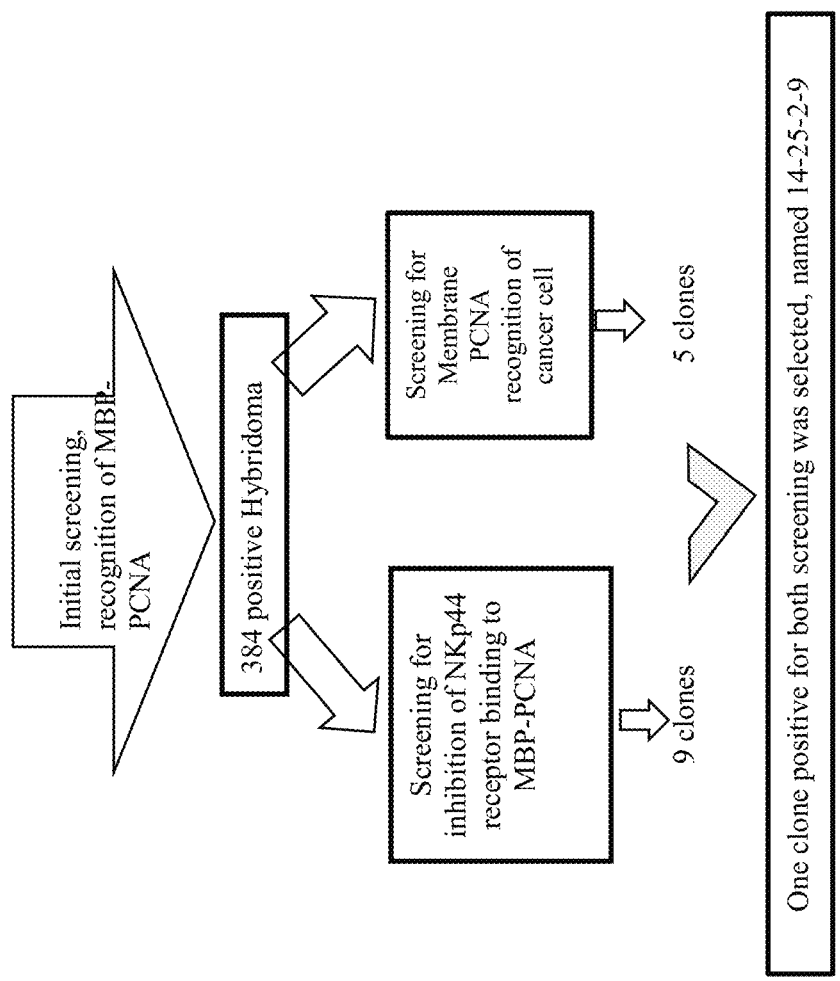
Figure 18A:
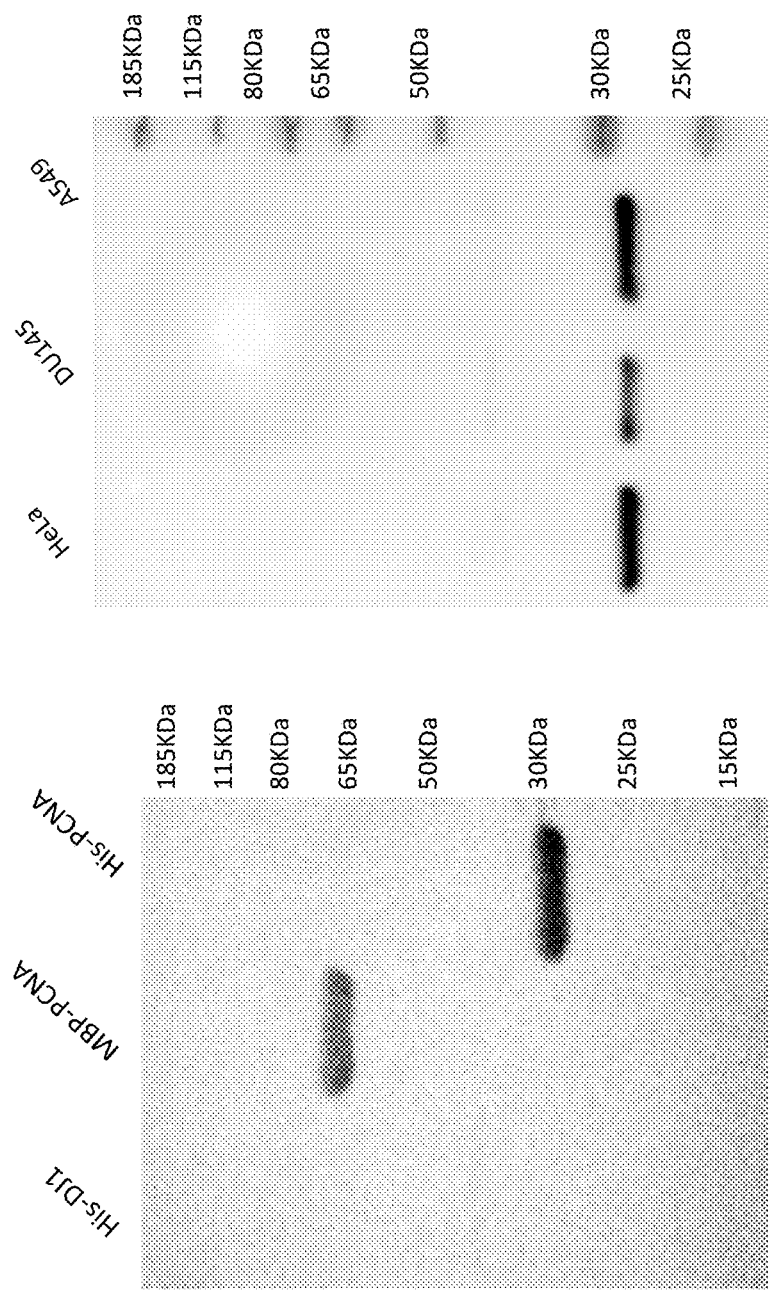
FIGS. 18A-18C includes (A) Western-blot result confirmed the specific recognition of recombinant PCNA by 13-10-1 (left panel). Recognition of cellular PCNA from three different cell lines by 14-25-9 and PC10 was also documented by western-blot (right panel). (B) A copy of the results shown in FIG. 4, with the addition from the same experiment of staining with 13-10-1. (C) Immunohistochemistry of human formalin fixed; paraffin embedded biopsy samples of oral cancer with 13-10-1 and PC10.
Figure 18B:
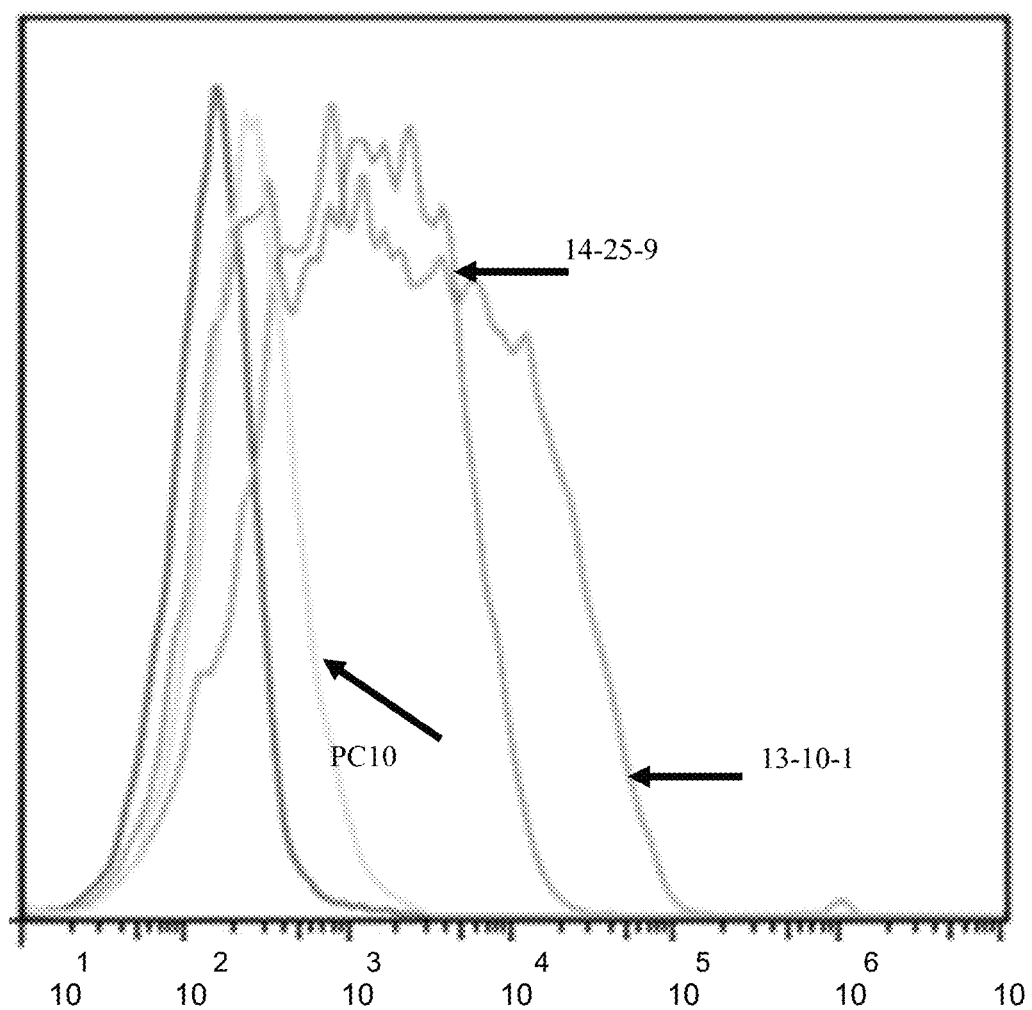
Figure 18C:
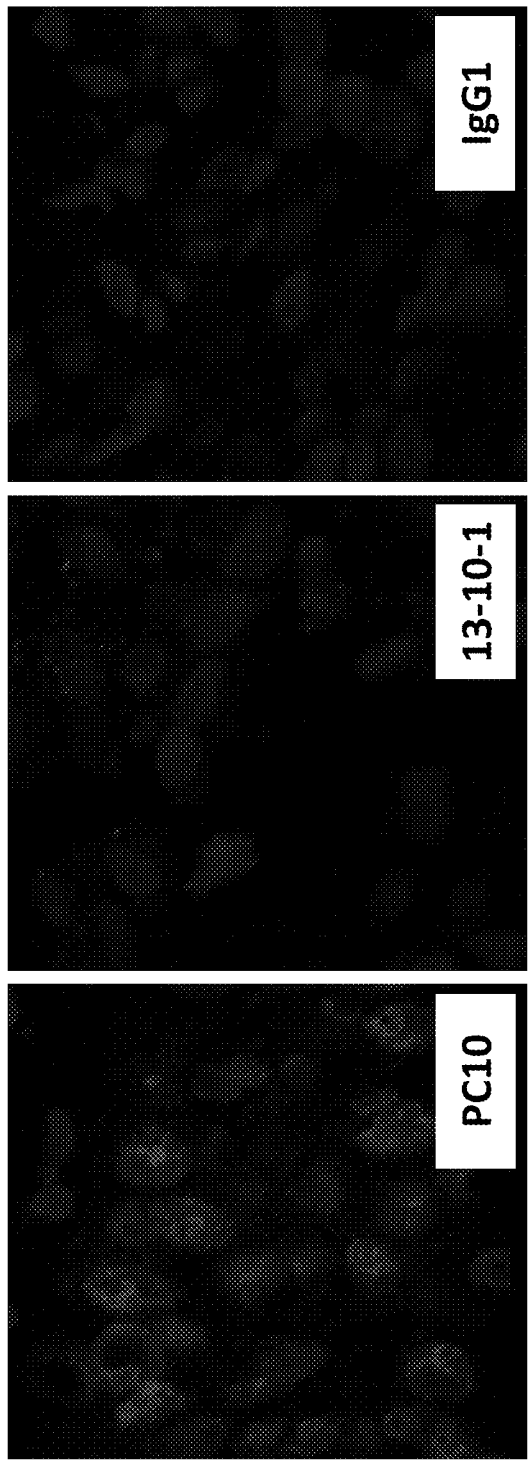
Figure 19:
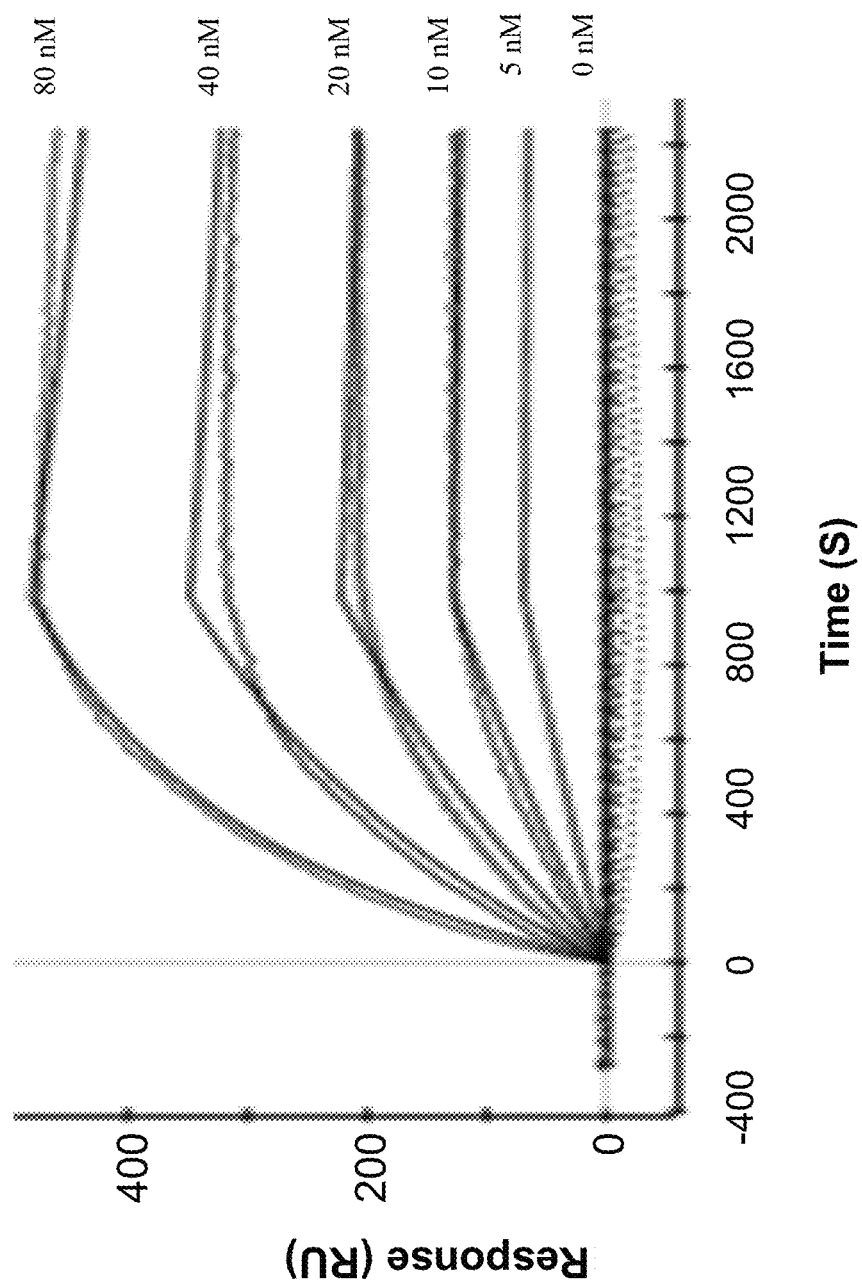
FIG. 19 is ProteOn array showing affinity of purified 13-10-1 for PCNA. Obtained values were: ka=1.10E$^{+4}$ (msec$^{-1}$); kd=9.90E$^{-5}$ (sec$^{-1}$); KD=8.99E$^{-9}$ M; Concentrations: 0-80 nM.

Hybridoma technology was used for the production of specific monoclonal antibodies against membranal PCNA. Immunization of five C57BL6 mice was done with His-PCNA (Human) in CFA as well as IFA according to the schematic shown in (FIG. 6A). During the immunization schedule at day 43 serum titter of anti PCNA polyclonal antibody was checked from every mouse and two of them were chosen according to their highest titter of the serum antibody. Splenocytes were then harvested from these two mice and fused with SP2/0 cells for the production of hybridoma (FIG. 6A). For the screening of the antibody of interest two approaches were taken one was inhibition of NKp44 receptor binding to MBP-PCNA in ELISA and the second was cancer cell surface PCNA recognition via FACS. From 384 total PCNA positive hybridoma one clone named 14-25-9 (short for 14-25-2-9) showed positive result for both screening (FIG. 1B-C). Using the same procedure, a second monoclonal antibody was produced—13-10-1, showing comparable binding capabilities to PCNA (FIGS. 18 and 19).

Example 6

Characterizing PCNA Binding Capabilities of the 14-25-9 mAb

Figures 7A, 7B, 7C:
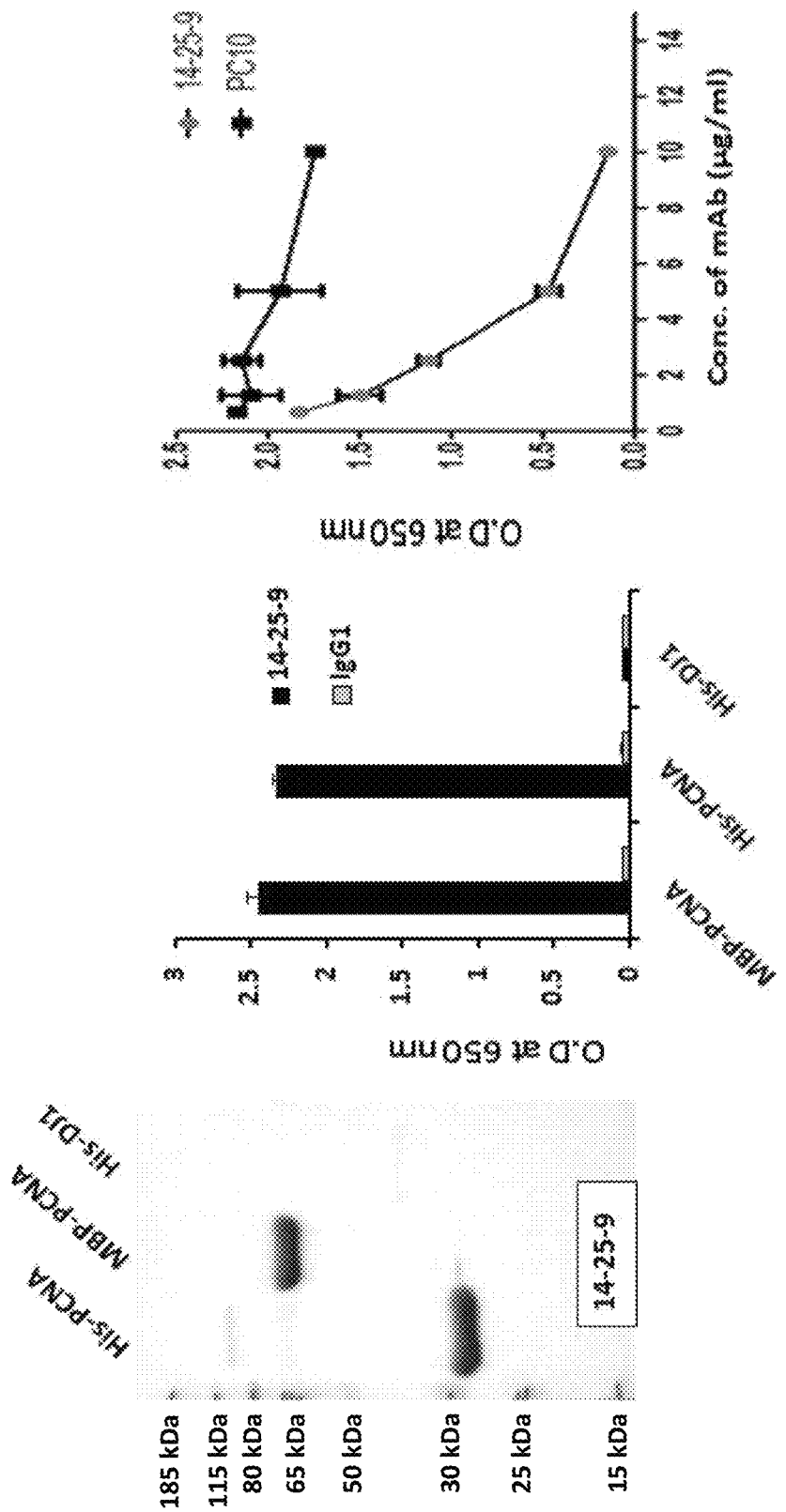
FIGS. 7A-7C. (A) Western blot result confirming the specific recognition of recombinant PCNA by 14-25-9. (B) ELISA result representing binding of FPLC purified monoclonal antibody 14-25-9 with MBP-PCNA, His-PCNA and unrelated protein His-DJ1, IgG1 is Isotype control. (C) ELISA result showing dose dependent inhibition of NKp44 receptor binding to PCNA by 14-25-9 as well as comparison with commercial anti PCNA mAb clone PC10.
Figures 8A, 8B:
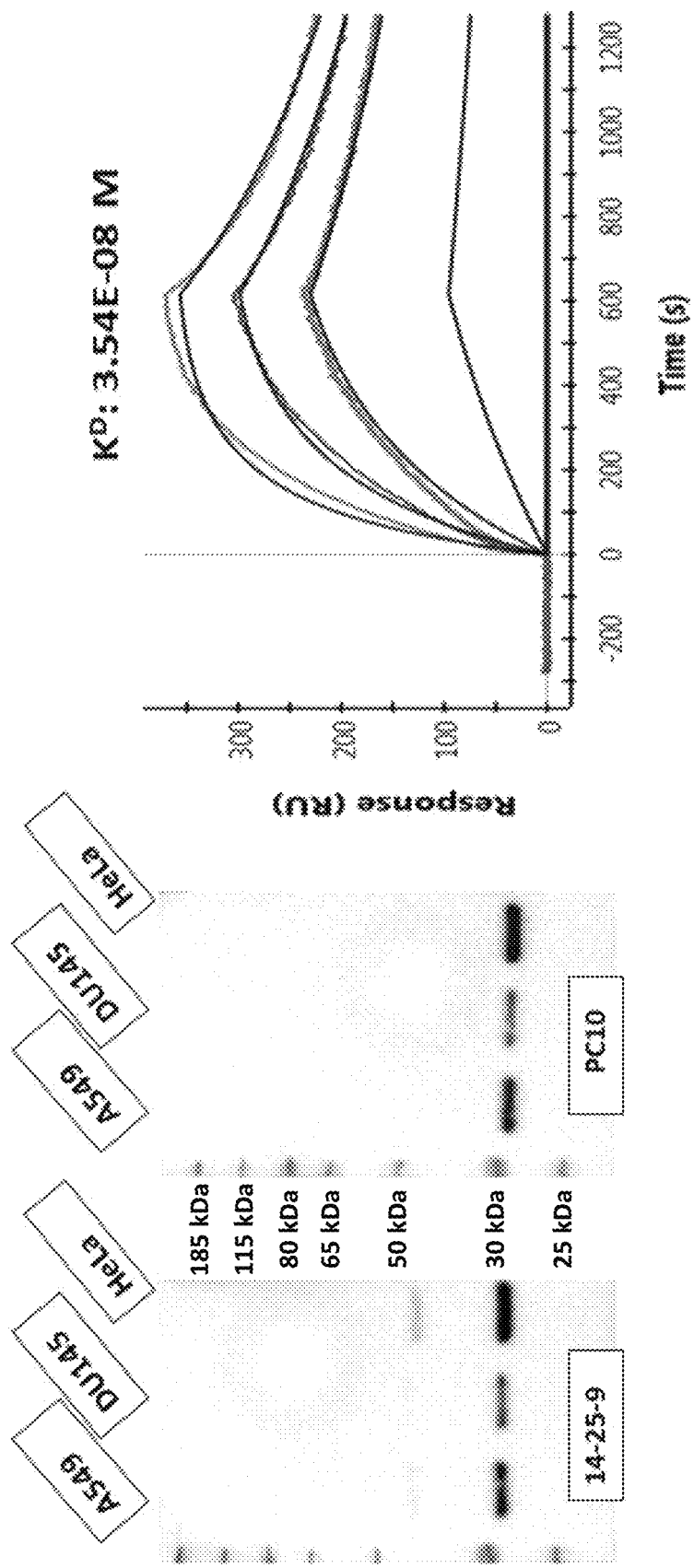
FIGS. 8A-8B. (A) Recognition of cellular PCNA from three different cell lines by 14-25-9 and PC10, represented via Western blot. (B) Affinity of purified 14-25-9 for PCNA, measured using ProteOn. Concentrations: 0-80 nM.

ELISA and western-blot were used to show significant binding of the 14-25-9 mAb with recombinant His and MBP tagged PCNA, compared to an unrelated protein His-DJ1 (FIG. 7A-B). Recognition of endogenous PCNA from several cancers cell lines by western-blot showed that 14-25-9 binds similarly like commercial anti PCNA mAb (clone PC10) (FIG. 8A). Binding affinity of 14-25-9 towards PCNA was determined using ProteOn and the KD value was found to be $3.54E^{-08}$ M (FIG. 8B). In a co-incubation of 14-25-9 or PC10 with chimeric NKp44 receptor Ig, only 14-25-9 showed strong inhibition of binding of NKp44 receptor Ig with PCNA (FIG. 7C). Inhibition of 14-25-9 was dose dependent, 10 μg/ml showed the highest inhibition.

Example 7

Cell Surface PCNA Recognition by the 14-25-9 mAb

Figure 9:
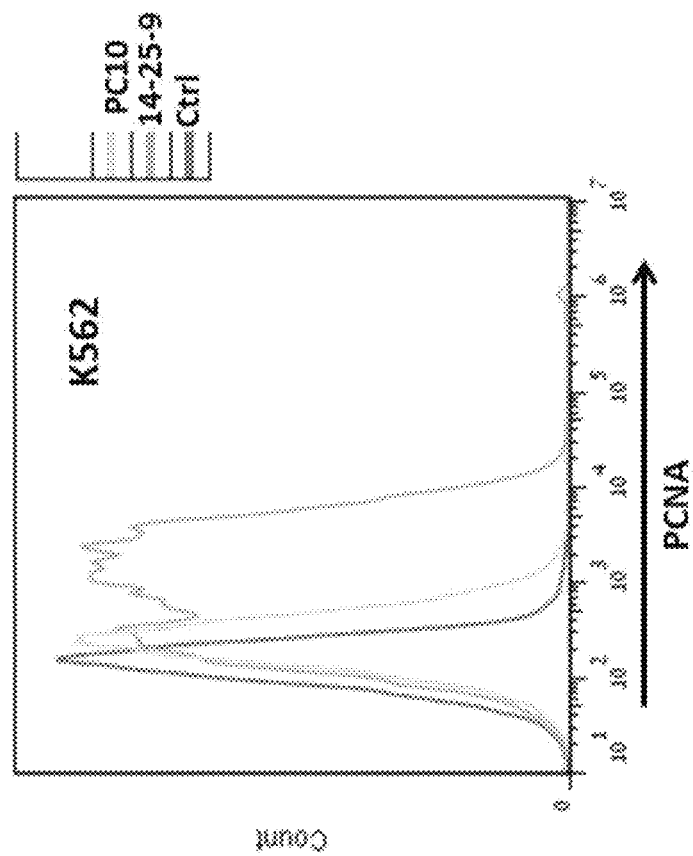
FIG. 9 is FACS staining showing membrane express PCNA recognition by purified 14-25-9 in live K562 cell line compared to commercial PC10 clone.
Figure 9:
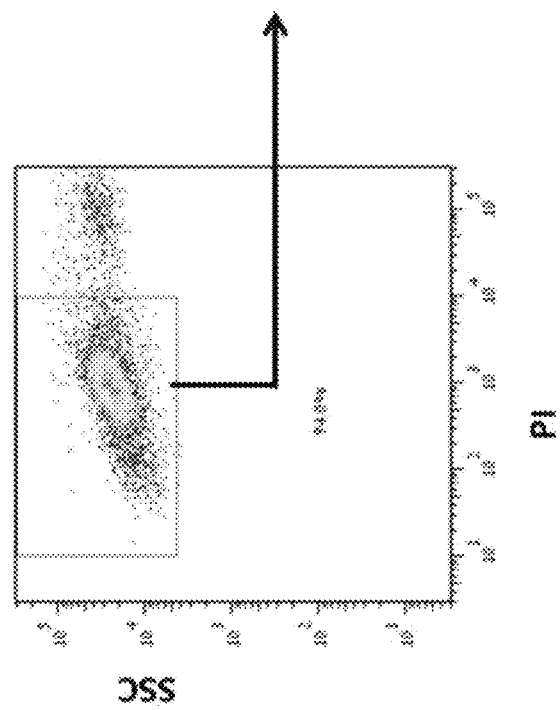
Figure 10A:
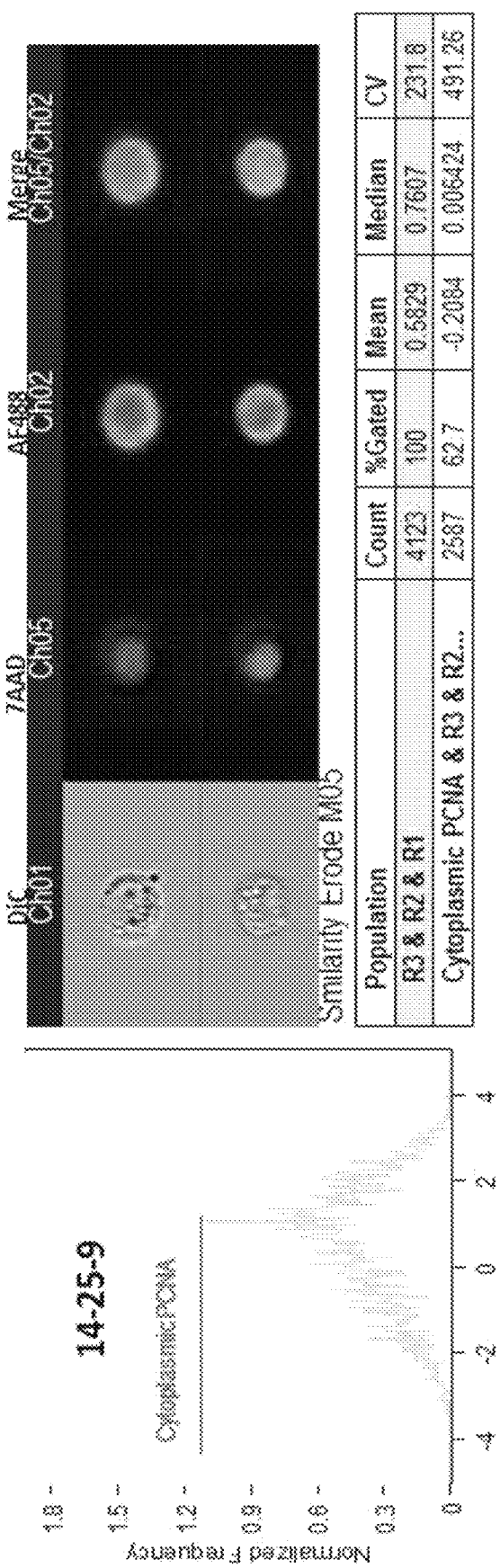
FIGS. 10A-10B presents image stream results (from HeLa cells) showing recognition of (A) mainly cytoplasmic PCNA by 14-25-9, whereas (B) PC10 binds with nuclear PCNA.
Figure 10B:
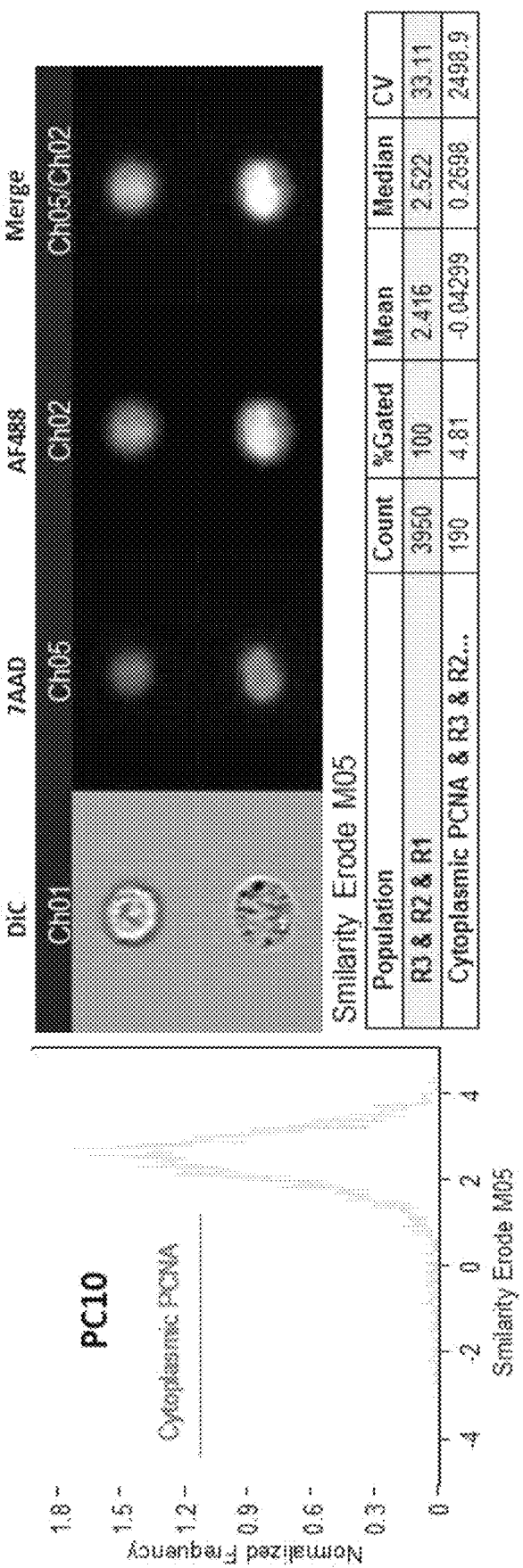

The following experiments were performed to test the ability of the 14-25-9 mAb to specifically recognize cell surface PCNA. Surface staining of several tumor cell lines e.g., K562 in FACS showed that 14-25-9 recognized cell surface PCNA where commercial clone PC10 showed almost no surface staining (FIG. 9). When intracellular distribution of PCNA was checked in an 'Image Stream' experiment, the inventors observed that 14-25-9 recognized mainly cytoplasmic PCNA whereas PC10 recognized nuclear PCNA of HeLa cells (FIG. 10).

Example 8

Figures 11A, 11B:
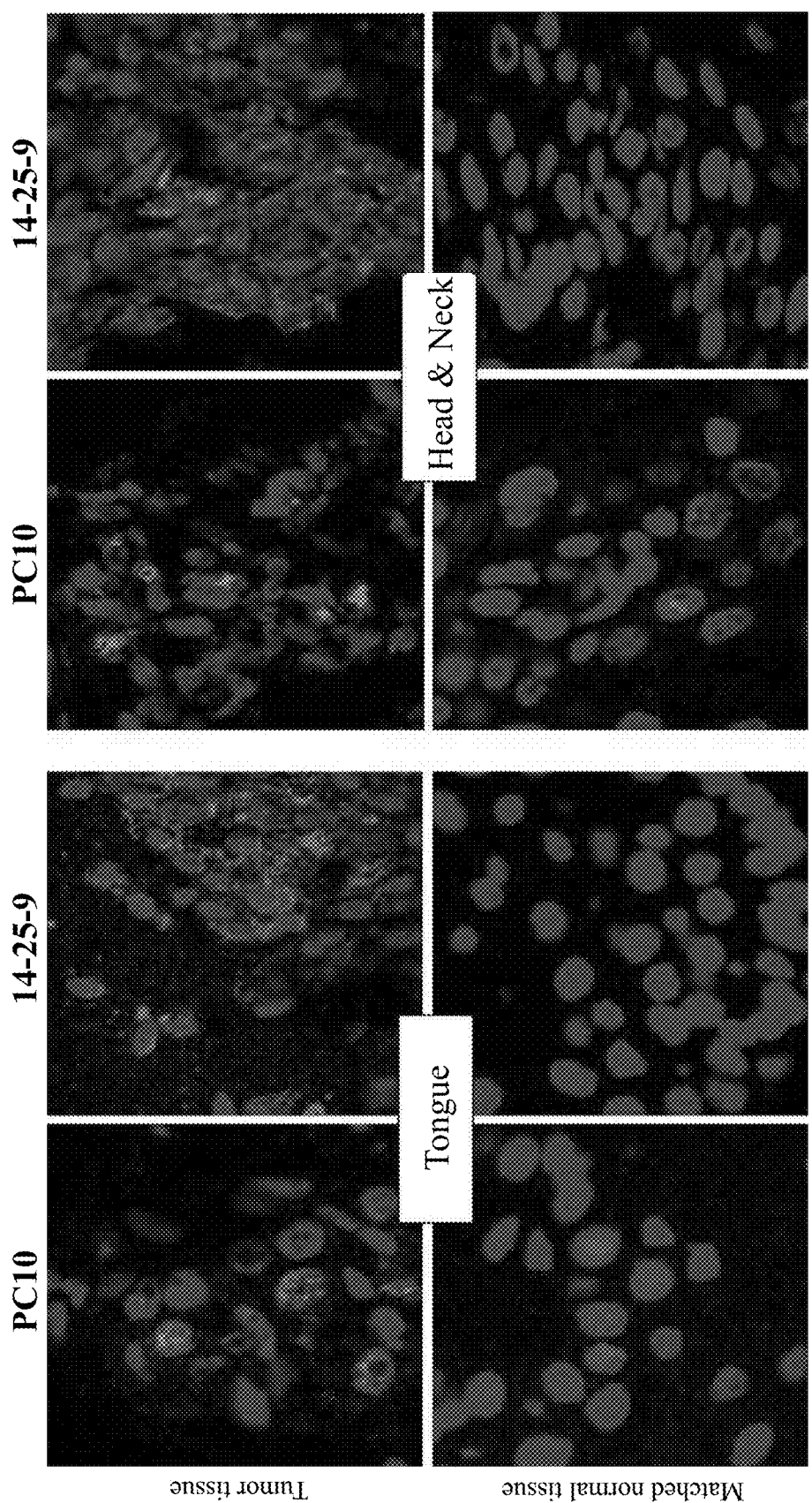
FIGS. 11A-11B is fluorescent immunohistochemistry micrographs of human formalin fixed normal and tumor tissues; paraffin embedded biopsy samples of (A) tongue and (B) head & neck with 14-25-9 and PC10.
Figures 12A, 12B:
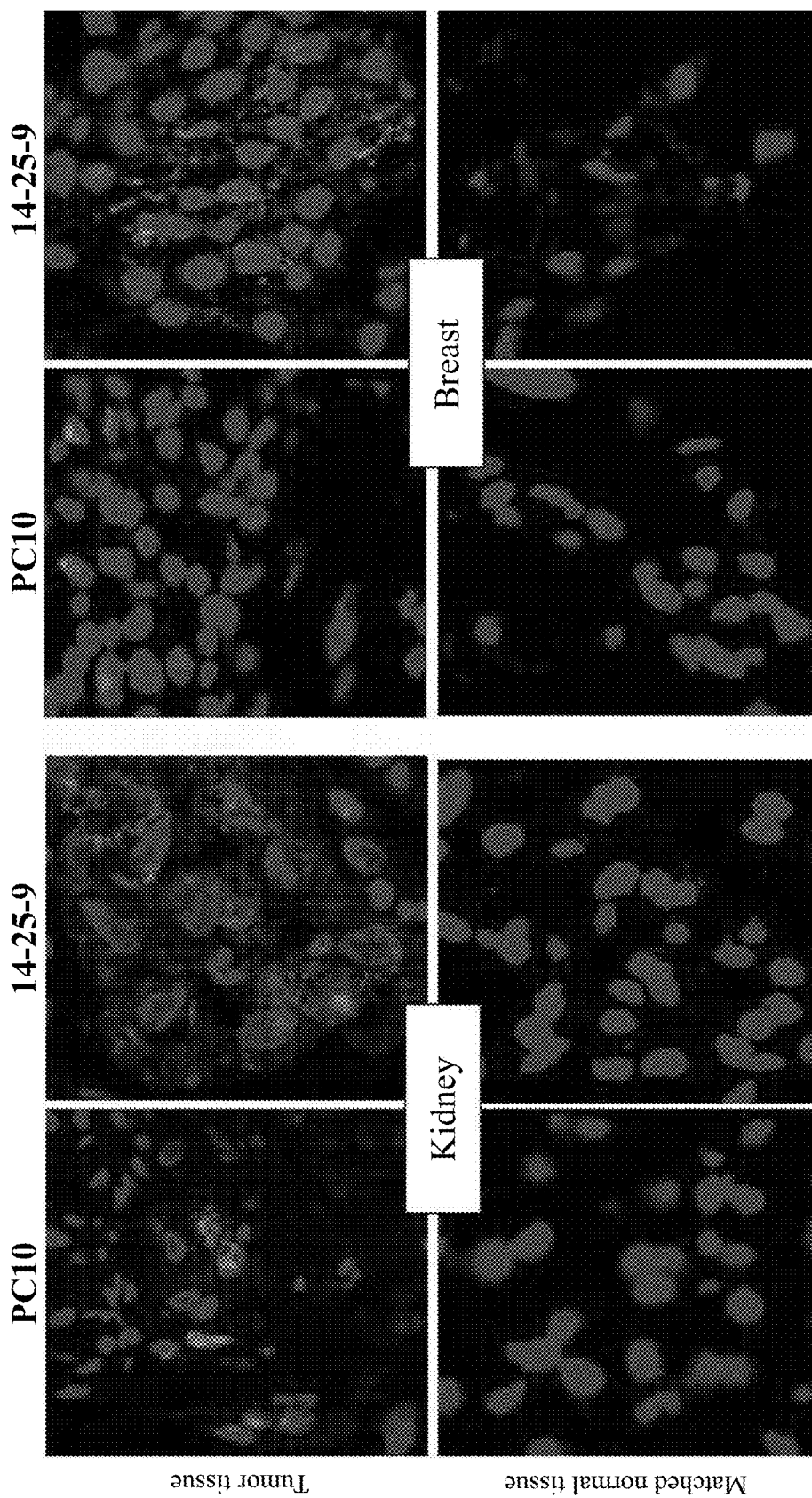
FIGS. 12A-12B is fluorescent immunohistochemistry micrographs of human formalin fixed normal and tumor tissues; paraffin embedded biopsy samples of (A) kidney and (B) breast with 14-25-9 and PC10.

The 14-25-9 mAb Recognizes Non-Nuclear PCNA from Cancer Tissues, but not from Patient-Matched Non-Cancerous Tissues The mAb 14-25-9 was also shown to bind to non-nuclear (cytoplasmic-membrane) PCNA in formalin-fixed paraffin-embedded (FFPE) human biopsy samples from cancer patients. In contrast, PC10 was shown to bind mostly to nuclear PCNA in those samples. Note that in matched non-cancerous samples from the same tissue of the same patient, 14-25-9 showed no staining while PC10 stained to a lesser extent the nuclear PCNA. This was observed using fluorescence immunohistochemistry of sections from FFPE blocks for human tongue and head & neck cancers (FIG. 11) and for kidney and breast cancers (FIG. 12).

Example 9

Figure 13A:
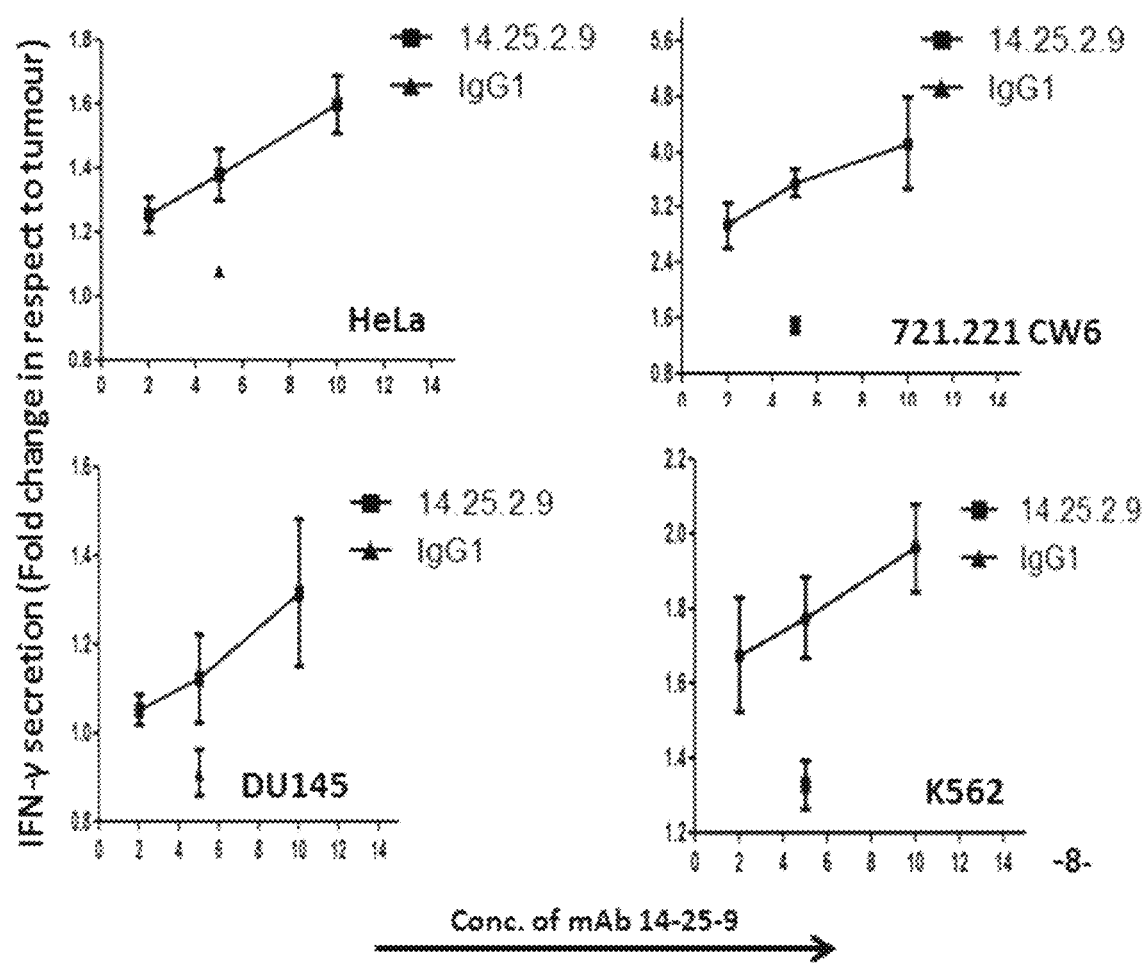
FIGS. 13A-13B includes graphs showing human NK activation by the 14-25-9 mAb. (A) Freshly isolated human NK cells were co-incubation of with different cancer cell lines from a solid tumor and from leukemia over-night (HeLa, DU145, 721.221 and K562) in the presence of 14-25-9 or IgG1 as control. NK cells that were incubated with 14-25-9 showed increased in IFN-γ release compared to mouse IgG1 as control. (B) Anti PCNA mAb 14-25-9 improved the lysis activity of fresh primary human NK cells when interacted with 721.221 CW6 in effector and target ratio of 1:3.
Figure 13B:
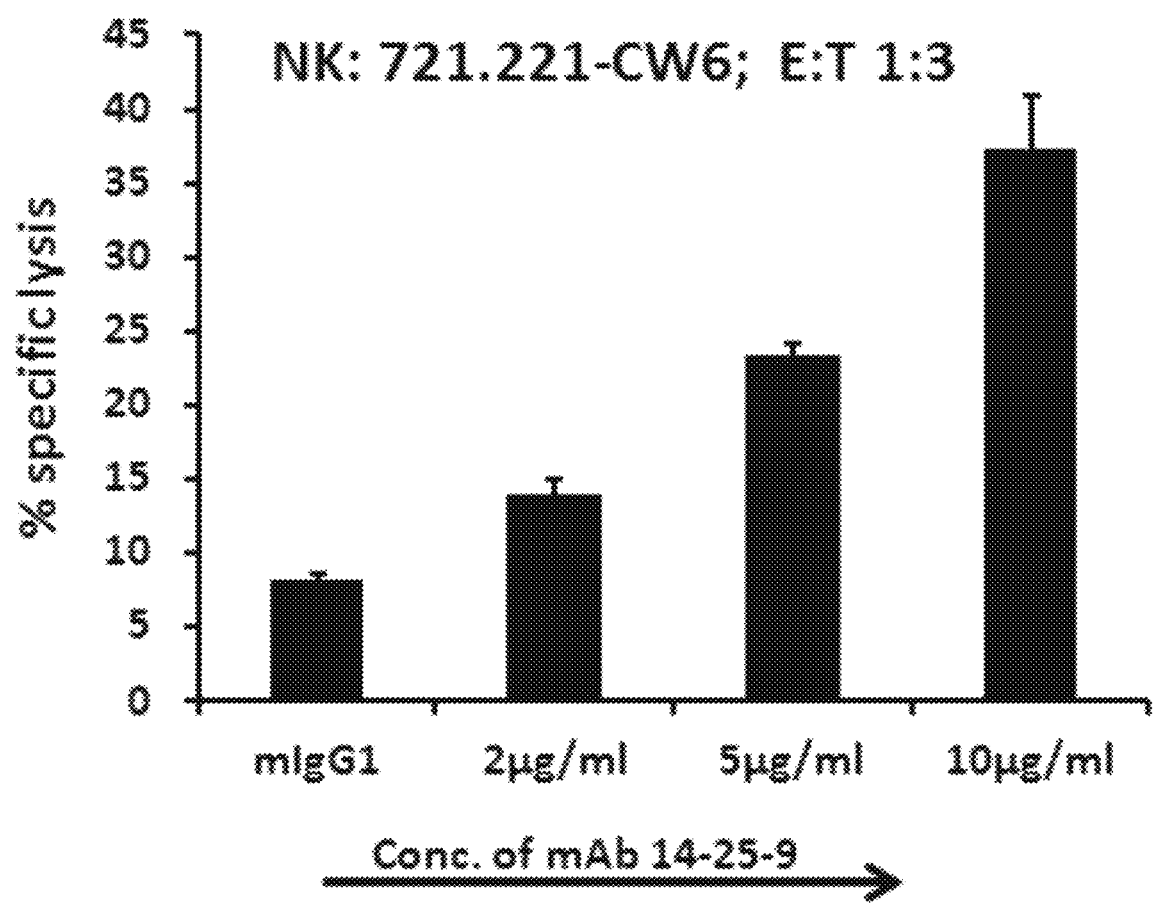

The Effect of the 14-25-9 mAb on the Capacity of Human NK Cells to Act on Cancer Cells To test the ability of the 14-25-9 mAb to activate human NK cells, the following experiment was performed. Freshly isolated human NK cells were co-incubated with different cancer cell lines from a solid tumor and from leukemia (HeLa, DU145, 721.221 and K562), over-night, in the presence of 14-25-9 or IgG1 (as control). NK cells that were incubated with 14-25-9 showed increase in IFN-γ release compared to mouse IgG1 control (FIG. 13A). Anti PCNA mAb 14-25-9 was also shown to be able to improve the lysis activity of fresh primary human NK cells when interacting with mainly 721.221 CW6 in effector and target ratio of 1:3 (FIG. 13B).

Example 10

In-Vivo Effect of 14-25-9 on Activation of NK Cells Against Tumors

Figure 14:
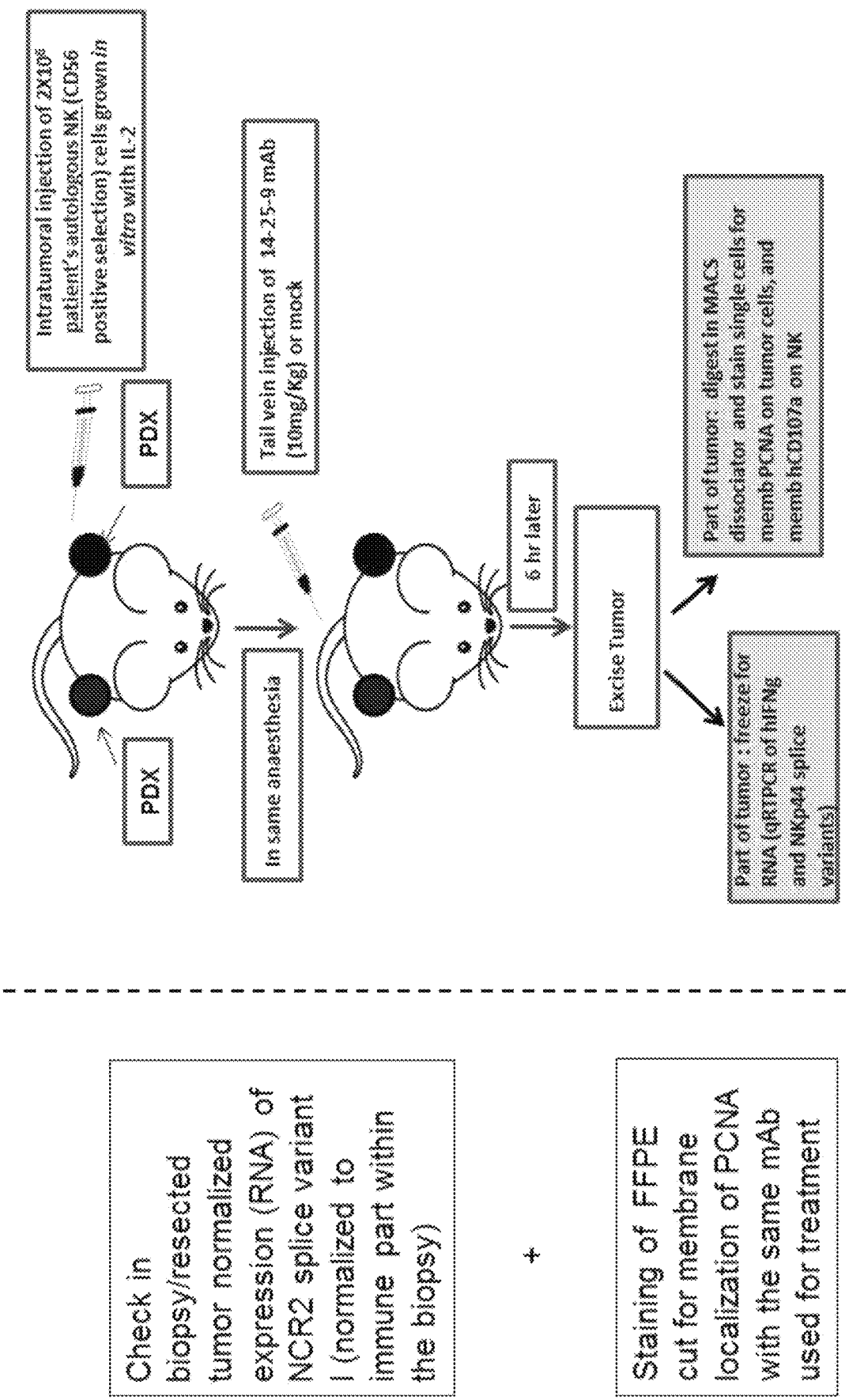
FIG. 14 is a non-limiting experimental scheme of in-vivo human NK activation against xenografts in Nude mice. (Left) Check biopsy/resected tumor normalized expression (RNA) of NCR2 splice variant I (normalized to immune part within the biopsy)+Staining of FFPE cut for membrane localization of PCNA with the same mAb used for the treatment. (Right) Patient derived xenograft (PDX): Intratumoral injection of 2×10⁶ patient's autologous NK (CD56 positive selection) cells grown in vitro with IL-2 into mice. In same anesthesia tail vein injection of 14-25-9 mAb (10 mg/Kg) or mock. Six (6) hr later excise tumor and: Part of tumor: freeze for RNA (qRTPCR of hiNg and NKp44 splice variants; another part of tumor: digest in MACS dissociator and stain single cells for memb PCNA on tumor cells, and memb hCD107a on NK.
Figure 15:
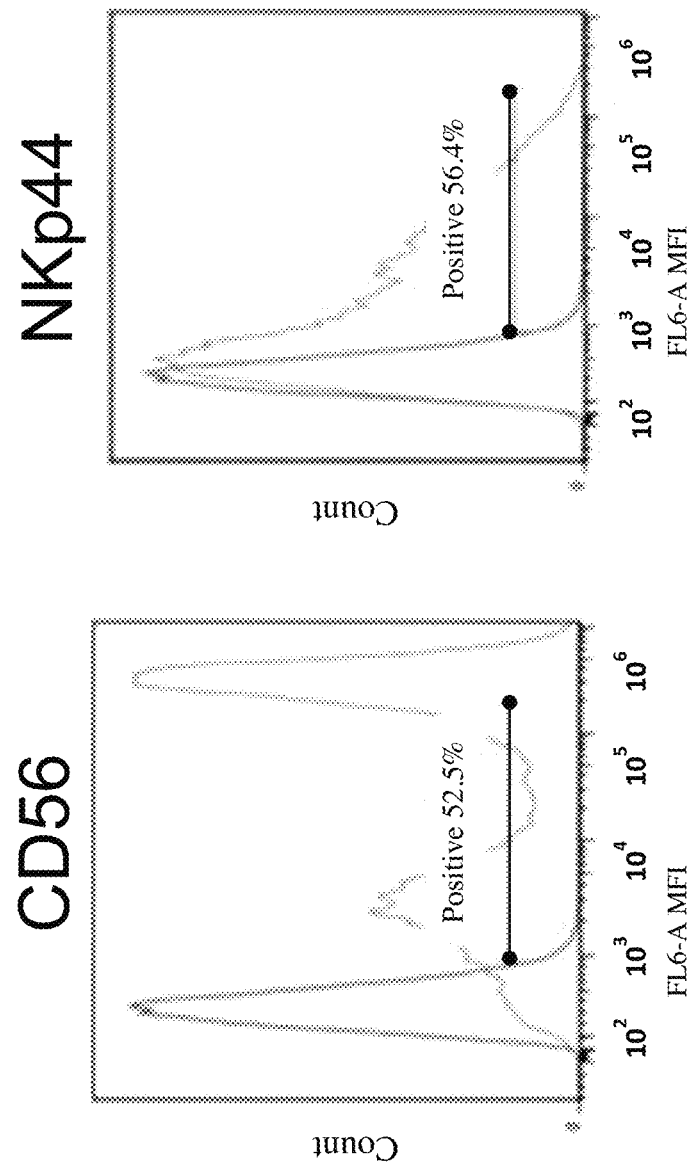
FIG. 15 is FACS staining of NK cells which were isolated from a patient's PBMC and propagated with IL-2. Staining with anti-human CD56 (left panel) showed the expected phenotype of NK cells expressing either moderate or high CD56 levels. Both NK cell types were positive for NKp44 expression (right panel). X axis—FL6-A MFI, base-10 log scale.
Figure 16:
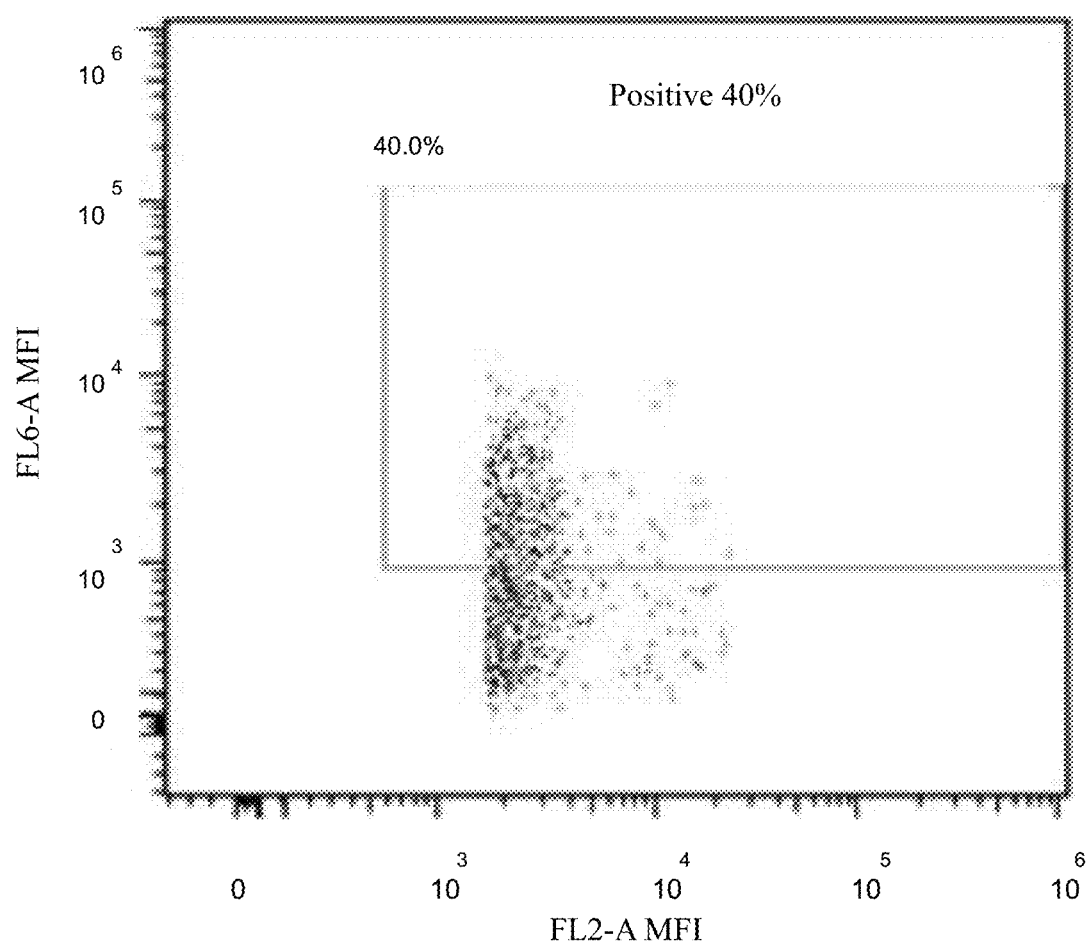
FIG. 16 is a FACS staining of human NK cells from harvested and solubilized patient derived xenografts stained the membrane expression of human CD107a. X axis—FL2-A MFI. Y axis—FL6-A-MFI. Both axes are in base-10 log scale.
Figure 17:
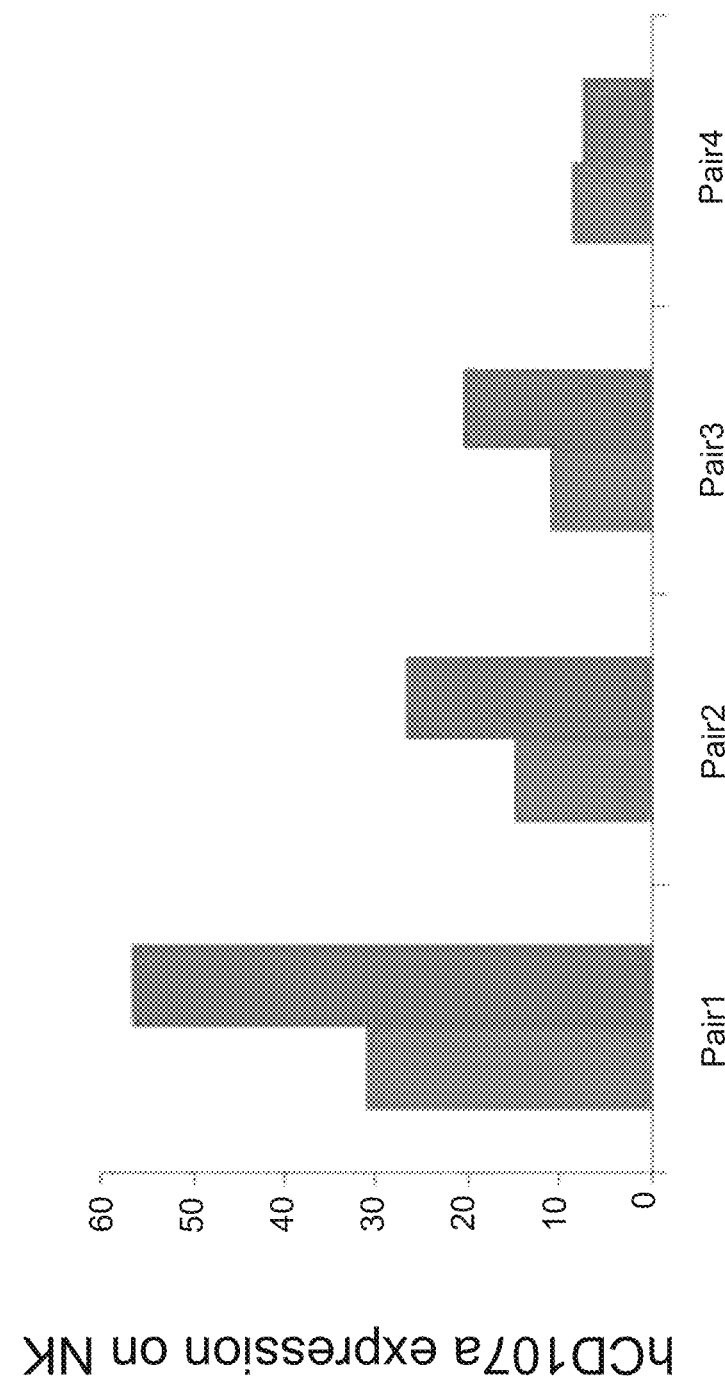
FIG. 17 is vertical bar charts comparisons of CD107a (NK Activation marker) comparing pairs of PDX bearing mice injected intra-PDX with autologous NK and treated IV with 14-25-9 or control treated mice.

For in-vivo validation of the activity of 14-25-9, immunocompromised NOD/SCID mice were used. Patient derived Xenografts (PDX) were grown in those mice and at the same time patient's autologous CD56+NK cells were grown in-vitro in culture. When the PDX were measurable, intra-tumoral injection of autologous NK was done and at the same time 14-25-9 was injected via tail vain (FIG. 14). Injected human NK cells contained both $CD56^{moderate}$ and $CD56^{high}$ cells (as expected) and were $NKp44^{positive}$ (FIG. 15). After 6 hr, PDX were harvested, solubilized and human CD107a expression was analyzed from gated $CD56^{positive}$ human NK cells (example in FIG. 16). Human NK cells in the PDX were activated by the 14-25-9 inoculation to the tail vein as can be seen by increase in CD107a expression compared to untreated mice (FIG. 17).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An antibody or an antigen-binding portion thereof, the antibody comprising three heavy chain CDRs (CDR-H) and three light chain CDRs (CDR-L), wherein:
   CDR-H1 comprises the amino acid sequences selected from SEQ ID NO: 11 (VYAFSS) and SEQ ID NO: 24 (SSWMN),
   CDR-H2 comprises the amino acid sequence as set forth in SEQ ID NO: 12 (RIYPADGDTN),
   CDR-H3 comprises the amino acid sequence as set forth in SEQ ID NO: 13 (WLRAMDY),
   CDR-L1 comprises the amino acid sequence as set forth in SEQ ID NO: 14 (KASQNVGTNVA),
   CDR-L2 comprises the amino acid sequence as set forth in SEQ ID NO: 15 (SASYRYS), and
   CDR-L3 comprises the amino acid sequence as set forth in SEQ ID NO: 16 (QQYNSYPYT); and wherein said antibody or antigen-binding portion thereof binds to PCNA.

2. The antibody or an antigen-binding portion thereof of claim 1, wherein CDR-H1 comprises or consists of the amino acid sequence as set forth in SEQ ID NO: 25 (VYAFSSWMN).

3. The antibody or an antigen-binding portion thereof of claim 1, wherein CDR-H2 comprises or consists of the amino acid sequence as set forth in SEQ ID NO: 26 (RIYPADGDTNYNGNFRG).

4. The antibody or an antigen-binding portion thereof of claim 1, comprising a variable region heavy chain comprising the amino acid sequence of SEQ ID NO: 17.

5. The antibody or an antigen-binding portion thereof of claim 1, comprising a variable region light chain comprising the amino acid sequence of SEQ ID NO: 18.

6. The antibody or an antigen-binding portion thereof of claim 1, comprising a constant region heavy chain comprising the amino acid sequence of SEQ ID NO: 19.

7. The antibody or an antigen-binding portion thereof of claim 1, comprising a constant region light chain comprising the amino acid sequence of SEQ ID NO: 20.

8. The antibody or an antigen-binding portion thereof of claim 1, wherein the antigen binding fragment is selected from the group consisting of a Fv, Fab, F(ab')$_2$, scFV or a scFV$_2$ fragment.

9. The antibody or an antigen-binding portion thereof of claim 1, having increased binding affinity to non-nuclear PCNA.

10. The antibody or an antigen-binding protein thereof of claim 1, having the ability to block the interaction between PCNA and NKp44-1.

11. A pharmaceutical composition comprising the antibody or an antigen-binding portion thereof of claim 1, and a pharmaceutically acceptable carrier.

12. A method for treating as subject suffering from a NKp44-1-associated disease or disorder the method comprising administering to said subject a therapeutically effective amount of the pharmaceutical composition comprising the antibody or an antigen-binding portion thereof of any claim 1 having: increased binding affinity to non-nuclear PCNA and the ability to block the interaction between PCNA and NKp44-1, and a pharmaceutically acceptable carrier.

13. The method of claim 12, wherein said NKp44-1-associated disease is cancer.

14. The method of claim 13, wherein said cancer is selected from the group consisting of prostate cancer, leukemia, kidney cancer, head and neck cancer, tongue cancer, and breast cancer.

15. A kit for detecting non-nuclear PCNA comprising an antibody or antigen-binding portion thereof of claim 1.

16. A method of detecting non-nuclear PCNA in a subject, comprising detecting in a sample derived from the subject whether non-nuclear PCNA is present in the sample by contacting sample with an anti-PCNA antibody of claim 1 and detecting the binding between the non-nuclear PCNA and the antibody.

17. The method of any one of claim 16, wherein the sample comprises a non-nuclear fraction.

18. A method of diagnosing an NKp44-1-associated disease in a subject, comprising detecting whether non-nuclear PCNA is present in a sample derived from the subject, by contacting the sample with the antibody of claim 1 and detecting binding between the non-nuclear PCNA and the antibody, wherein the presence of PCNA in the sample is indicative of a NKp44-1-associated disease in the subject.

19. The method of any one of claim 18, wherein the sample comprises a non-nuclear fraction.

* * * * *

SEQUENCE LISTING

```
<160> NUMBER OF SEQ ID NOS: 35

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Gly Phe Ser Phe Asn Ile
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Arg Ile Arg Ser Lys Ser Asn Asn Tyr Ala Thr Tyr
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic
```

```
<400> SEQUENCE: 3

His Pro Asn Tyr Ser Gly Phe Asn Tyr Pro Phe Ala Ser
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Arg Ser Ser Gln Ser Ile Val His Ser Asn Gly Lys Thr Tyr Phe Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Phe Gln Gly Ser His Val Pro Tyr Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic

<400> SEQUENCE: 7

Lys Leu Val Glu Ser Gly Gly Gly Leu Val Gln Pro Thr Gly Ser Leu
1               5                   10                  15

Lys Leu Ser Cys Val Thr Ser Gly Phe Ser Phe Asn Ile Tyr Ala Met
            20                  25                  30

Asn Trp Val Arg Gln Ala Pro Gly Lys Gly Leu Glu Trp Val Ala Arg
        35                  40                  45

Ile Arg Ser Lys Ser Asn Asn Tyr Ala Thr Tyr Tyr Ala Asp Ser Val
    50                  55                  60

Lys Asp Arg Phe Thr Ile Ser Arg Asp Asp Ser Glu Ser Met Leu Tyr
65                  70                  75                  80

Leu Gln Met Asn Asn Leu Lys Thr Glu Asp Thr Ala Met Tyr Tyr Cys
                85                  90                  95

Met Arg His Pro Asn Tyr Ser Gly Phe Asn Tyr Pro Phe Ala Ser Trp
            100                 105                 110

Gly Pro Gly Thr Leu Val Thr Val Ser Ala
        115                 120
```

```
<210> SEQ ID NO 8
<211> LENGTH: 112
<212> TYPE: PRT
<213> ORGANISM: Artificial Sequence
<220> FEATURE:
<223> OTHER INFORMATION: Synthetic

<400> SEQUENCE: 8

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Lys Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 9
<211> LENGTH: 324
<212> TYPE: PRT
<213> ORGANISM: Artificial Sequence
<220> FEATURE:
<223> OTHER INFORMATION: Synthetic

<400> SEQUENCE: 9

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205
```

-continued

```
Ile Glu Lys Thr Ile Ser Lys Thr Lys Gly Arg Pro Lys Ala Pro Gln
    210                 215                 220
Val Tyr Thr Ile Pro Pro Lys Glu Gln Met Ala Lys Asp Lys Val
225                 230                 235                 240
Ser Leu Thr Cys Met Ile Thr Asn Phe Phe Pro Glu Asp Ile Thr Val
                245                 250                 255
Glu Trp Gln Trp Asn Gly Gln Pro Ala Glu Asn Tyr Lys Asn Thr Gln
                260                 265                 270
Pro Ile Met Asp Thr Asp Gly Ser Tyr Phe Val Tyr Ser Lys Leu Asn
            275                 280                 285
Val Gln Lys Ser Asn Trp Glu Ala Gly Asn Thr Phe Thr Cys Ser Val
        290                 295                 300
Leu His Glu Gly Leu His Asn His His Thr Glu Lys Ser Leu Ser His
305                 310                 315                 320
Ser Pro Gly Lys
```

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

```
Arg Ala Asp Ala Ala Pro Thr Val Ser Ile Phe Pro Pro Ser Ser Glu
1               5                   10                  15
Gln Leu Thr Ser Gly Gly Ala Ser Val Val Cys Phe Leu Asn Asn Phe
            20                  25                  30
Tyr Pro Lys Asp Ile Asn Val Lys Trp Lys Ile Asp Gly Ser Glu Arg
        35                  40                  45
Gln Asn Gly Val Leu Asn Ser Trp Thr Asp Gln Asp Ser Lys Asp Ser
    50                  55                  60
Thr Tyr Ser Met Ser Ser Thr Leu Thr Leu Thr Lys Asp Glu Tyr Glu
65                  70                  75                  80
Arg His Asn Ser Tyr Thr Cys Glu Ala Thr His Lys Thr Ser Thr Ser
                85                  90                  95
Pro Ile Val Lys Ser Phe Asn Arg Asn Glu Cys
            100                 105
```

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

```
Val Tyr Ala Phe Ser Ser
1               5
```

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

```
Arg Ile Tyr Pro Ala Asp Gly Asp Thr Asn
```

-continued

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Trp Leu Arg Ala Met Asp Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Lys Ala Ser Gln Asn Val Gly Thr Asn Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Ser Ala Ser Tyr Arg Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Ser Tyr Pro Tyr Thr
1               5

<210> SEQ ID NO 17
<211> LENGTH: 104
<212> TYPE: PRT
<213> ORGANISM: Artificial Sequence
<220> FEATURE:
<223> OTHER INFORMATION: Synthetic

<400> SEQUENCE: 17

Glu Pro Gly Ala Ser Val Lys Ile Ser Cys Lys Ala Ser Val Tyr Ala
1               5                   10                  15

Phe Ser Ser Ser Trp Met Asn Trp Val Lys Gln Arg Pro Gly Lys Gly
                20                  25                  30

Leu Glu Trp Ile Gly Arg Ile Tyr Pro Ala Asp Gly Asp Thr Asn Tyr
            35                  40                  45

Asn Gly Asn Phe Arg Gly Lys Ala Thr Leu Thr Ala Asp Lys Ser Ser
        50                  55                  60

Ser Thr Ala Tyr Met Gln Leu Ser Ser Leu Thr Ser Glu Asp Ser Ala
65                  70                  75                  80

Val Tyr Phe Cys Ala Arg Trp Leu Arg Ala Met Asp Tyr Trp Gly Gln
                85                  90                  95

Gly Thr Ser Val Thr Val Ser Ser
            100

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

Asp Ile Val Met Thr Gln Ser Gln Lys Ile Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Ser Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 19
<211> LENGTH: 325
<212> TYPE: PRT
<213> ORGANISM: Artificial Sequence
<220> FEATURE:
<223> OTHER INFORMATION: Synthetic

<400> SEQUENCE: 19

Ala Lys Thr Thr Tyr Pro Pro Ser Val Tyr Pro Leu Ala Pro Gly Ser
1               5                   10                  15

Ala Ala Gln Thr Asn Ser Met Val Thr Leu Gly Cys Leu Val Lys Gly
            20                  25                  30

Tyr Phe Pro Glu Pro Val Thr Val Thr Trp Asn Ser Gly Ser Leu Ser
        35                  40                  45

Ser Gly Val His Thr Phe Pro Ala Val Leu Gln Ser Asp Leu Tyr Thr
    50                  55                  60

Leu Ser Ser Ser Val Thr Val Pro Ser Ser Thr Trp Pro Ser Glu Thr
65                  70                  75                  80

Val Thr Cys Asn Val Ala His Pro Ala Ser Ser Thr Lys Val Asp Lys
                85                  90                  95

Lys Ile Val Pro Arg Asp Cys Gly Cys Lys Pro Cys Ile Cys Thr Val
            100                 105                 110

Pro Glu Val Ser Ser Val Phe Ile Phe Pro Pro Lys Pro Lys Asp Val
        115                 120                 125

Leu Thr Ile Thr Leu Thr Pro Lys Val Thr Cys Val Val Val Asp Ile
    130                 135                 140

Ser Lys Asp Asp Pro Glu Val Gln Phe Ser Trp Phe Val Asp Asp Val
145                 150                 155                 160

Glu Val His Thr Ala Gln Thr Gln Pro Arg Glu Glu Gln Phe Asn Ser
                165                 170                 175

```
Thr Phe Arg Ser Val Ser Glu Leu Pro Ile Met His Gln Asp Trp Leu
            180                 185                 190

Asn Gly Lys Glu Phe Lys Cys Arg Val Asn Ser Ala Ala Phe Pro Ala
        195                 200                 205

Pro Ile Glu Lys Thr Ile Ser Lys Thr Lys Gly Arg Pro Lys Ala Pro
    210                 215                 220

Gln Val Tyr Thr Ile Pro Pro Lys Glu Gln Met Ala Lys Asp Lys
225                 230                 235                 240

Val Ser Leu Thr Cys Met Ile Thr Asp Phe Phe Pro Glu Asp Ile Thr
                245                 250                 255

Val Glu Trp Gln Trp Asn Gly Gln Pro Ala Glu Asn Tyr Lys Asn Thr
            260                 265                 270

Gln Pro Ile Met Asp Thr Asp Gly Ser Tyr Phe Val Tyr Ser Lys Leu
        275                 280                 285

Asn Val Gln Lys Ser Asn Trp Glu Ala Gly Asn Thr Phe Thr Cys Ser
    290                 295                 300

Val Leu His Glu Gly Leu His Asn His His Thr Glu Lys Ser Leu Ser
305                 310                 315                 320

His Ser Pro Gly Lys
                325

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 21
<211> LENGTH: 5
<212> TYPE: PRT
<213> ORGANISM: Artificial Sequence
<220> FEATURE:
<223> OTHER INFORMATION: Synthetic

<400> SEQUENCE: 21

Ile Tyr Ala Met Asn
1               5

<210> SEQ ID NO 22
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 22

Gly Phe Ser Phe Asn Ile Tyr Ala Met Asn
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

Arg Ile Arg Ser Lys Ser Asn Asn Tyr Ala Thr Tyr Tyr Ala Asp Ser
1               5                   10                  15

Val Lys Asp

<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Ser Ser Trp Met Asn
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Val Tyr Ala Phe Ser Ser Ser Trp Met Asn
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic

<400> SEQUENCE: 26

Arg Ile Tyr Pro Ala Asp Gly Asp Thr Asn Tyr Asn Gly Asn Phe Arg
1               5                   10                  15

Gly

<210> SEQ ID NO 27
<211> LENGTH: 322
<212> TYPE: DNA
<213> ORGANISM: Artificial Sequence
<220> FEATURE:
<223> OTHER INFORMATION: Synthetic

<400> SEQUENCE: 27
tgacattgtg atgactcagt ctcaaaaaat catgtccaca tcagtaggag acagggtcag      60
cgtcacctgc aaggccagtc agaatgtggg tactaatgta gcctggtatc aacagaaacc     120
```

```
aggcaatct cctaaagtac tgatttactc ggcatcctac cggtacagtg gagtccctga    180
tcgcttcaca ggcagtggat ctgggacaga tttcactctc agcatcagca atgtgcagtc    240
tgaagacttg gcagagtatt tctgtcagca atataacagc tatccgtaca cgttcggagg    300
ggggaccaag ctggaaataa aa                                             322

<210> SEQ ID NO 28
<211> LENGTH: 325
<212> TYPE: DNA
<213> ORGANISM: Artificial Sequence
<220> FEATURE:
<223> OTHER INFORMATION: Synthetic

<400> SEQUENCE: 28
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga acagttggac tgatcaggac    180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg ttaga                                          325

<210> SEQ ID NO 29
<211> LENGTH: 312
<212> TYPE: DNA
<213> ORGANISM: Artificial Sequence
<220> FEATURE:
<223> OTHER INFORMATION: Synthetic

<400> SEQUENCE: 29
gagcctgggg cctcagtgaa gatttcctgc aaggcttctg tctacgcatt cagtagttcc     60
tggatgaact gggtgaagca gaggcctgga aagggtcttg agtggattgg acggatttat    120
cctgcagatg gagatactaa ctacaatggg aacttcaggg gcaaggccac actgactgca    180
gacaaatcct ccagcacagc ctacatgcaa ctcagcagtc tgacatctga ggactctgcg    240
gtctacttct gtgcaagatg gttacgggct atggactact ggggtcaagg aacctcagtc    300
accgtctcct ca                                                        312

<210> SEQ ID NO 30
<211> LENGTH: 978
<212> TYPE: DNA
<213> ORGANISM: Artificial Sequence
<220> FEATURE:
<223> OTHER INFORMATION: Synthetic

<400> SEQUENCE: 30
gccaaaacaa catacccccc atctgtctat ccactggccc ctggatctgc tgcccaaact     60
aactccatgg tgaccctggg atgcctggtc aagggctatt tccctgagcc agtgacagtg    120
acctggaact ctggatccct gtccagcggt gtgcacacct tccagctgt cctgcagtct    180 gacctctaca ctctgagcag ctcagtgact gtcccctcca gcacctggcc cagcgagacc    240
gtcacctgca acgttgccca cccggccagc agcaccaagg tggacaagaa aattgtgccc    300
agggattgtg gttgtaagcc ttgcatatgt acagtcccag aagtatcatc tgtcttcatc    360 ttcccccaa agcccaagga tgtgctcacc attactctga ctcctaaggt cacgtgtgtt    420
gtggtagaca tcagcaagga tgatcccgag gtccagttca gctggtttgt agatgatgtg    480
gaggtgcaca cagctcagac gcaacccgg gaggagcagt tcaacagcac tttccgctca    540
```

```
gtcagtgaac ttcccatcat gcaccaggac tggctcaatg caaggagtt caaatgcagg      600 gtcaacagtg cagctttccc tgcccccatc gagaaaacca tctccaaaac caaaggcaga     660
ccgaaggctc acaggtgta caccattcca cctcccaagg agcagatggc caaggataaa      720
gtcagtctga cctgcatgat aacagacttc ttccctgaag acattactgt ggagtggcag     780
tggaatgggc agccagcgga gaactacaag aacactcagc ccatcatgga cacagatggc     840
tcttacttcg tctacagcaa gctcaatgtg cagaagagca ctgggaggc aggaaatact      900 ttcacctgct ctgtgttaca tgagggcctg cacaaccacc atactgagaa gagcctctcc     960
cactctcctg gtaaatga                                                   978
```

<210> SEQ ID NO 31
<211> LENGTH: 337
<212> TYPE: DNA
<213> ORGANISM: Artificial Sequence
<220> FEATURE:
<223> OTHER INFORMATION: Synthetic

<400> SEQUENCE: 31

```
tgatgttgtg atgacccaaa ctccgctctc cctgcctgtc agtcttggag atcaagcctc      60
catctcttgc agatctagtc agagcattgt acatagtaat ggaaagacct attttgaatg     120
gtaccttcag aaaccaggcc agtctccaaa gctcctgatc tacaaagttt ccaaccgatt     180
ttctggggtc ccagacaggt tcagtggcag tggatcaggg acagaattca cactcaagat     240
cagcagagtg gaggctgagg atctgggagt ttattactgc tttcaaggtt cacatgttcc     300
gtacacgttc ggaggggga ccaagctgga aataaaa                               337
```

<210> SEQ ID NO 32
<211> LENGTH: 324
<212> TYPE: DNA
<213> ORGANISM: Artificial Sequence
<220> FEATURE:
<223> OTHER INFORMATION: Synthetic

<400> SEQUENCE: 32

```
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga acgttggac tgatcaggac     180 agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg ttag                                            324
```

<210> SEQ ID NO 33
<211> LENGTH: 366
<212> TYPE: DNA
<213> ORGANISM: Artificial Sequence
<220> FEATURE:
<223> OTHER INFORMATION: Synthetic

<400> SEQUENCE: 33

```
aagctggtgg agtctggtgg aggattggtg cagcctacag ggtcattgaa actctcatgt      60
gtaacctctg gattcagttt caatatctac gccatgaact gggtccgcca ggctccagga     120
aagggtttgg aatgggttgc tcgcataaga agtaaaagta ataattatgc aacatattat     180
gccgattcag tgaaagacag attcaccatc tccagagatg attcagaaag catgctctat     240
```

```
ctccaaatga caacttgaaa aactgaggac acagccatgt attactgtat gagacacccc    300
aattactccg gctttaacta cccgtttgct tcctggggcc cagggactct ggtcactgtc    360
tctgca                                                                366
```

<210> SEQ ID NO 34
<211> LENGTH: 975
<212> TYPE: DNA
<213> ORGANISM: Artificial Sequence
<220> FEATURE:
<223> OTHER INFORMATION: Synthetic

<400> SEQUENCE: 34

```
gccaaaacga cacccccatc tgtctatcca ctggcccctg atctgctgcc caaactaac     60 tccatggtga ccctgggatg cctggtcaag ggctatttcc ctgagccagt gacagtgacc    120
tggaactctg gatccctgtc cagcggtgtg cacaccttcc cagctgtcct gcagtctgac    180
ctctacactc tgagcagctc agtgactgtc ccctccagca cctggcccag ccagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc ctaaggtcac gtgtgttgtg    420
gtagacatca gcaaggatga tcccgaggtc cagttcagct ggtttgtaga tgatgtggag    480
gtgcacacag ctcagacgaa accccgggag gagcagatca cagcactttt ccgttcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac aaacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aatga                                                     975
```

<210> SEQ ID NO 35
<211> LENGTH: 276
<212> TYPE: PRT
<213> ORGANISM: Homo sapiens

<400> SEQUENCE: 35

```
Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
            20                  25                  30

Gly Gln Thr Leu Thr Val Arg Cys Gln Tyr Pro Pro Thr Gly Ser Leu
        35                  40                  45

Tyr Glu Lys Lys Gly Trp Cys Lys Glu Ala Ser Ala Leu Val Cys Ile
    50                  55                  60

Arg Leu Val Thr Ser Ser Lys Pro Arg Thr Met Ala Trp Thr Ser Arg
65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110
```

-continued

```
Arg Pro Ser Asp Asn Ser Val Ser Lys Ser Val Arg Phe Tyr Leu Val
        115                 120                 125
Val Ser Pro Ala Ser Ala Ser Thr Gln Thr Ser Trp Thr Pro Arg Asp
    130                 135                 140
Leu Val Ser Ser Gln Thr Gln Thr Gln Ser Cys Val Pro Pro Thr Ala
145                 150                 155                 160
Gly Ala Arg Gln Ala Pro Glu Ser Pro Ser Thr Ile Pro Val Pro Ser
                165                 170                 175
Gln Pro Gln Asn Ser Thr Leu Arg Pro Gly Pro Ala Ala Pro Ile Ala
            180                 185                 190
Leu Val Pro Val Phe Cys Gly Leu Leu Val Ala Lys Ser Leu Val Leu
        195                 200                 205
Ser Ala Leu Leu Val Trp Trp Gly Asp Ile Trp Trp Lys Thr Met Met
    210                 215                 220
Glu Leu Arg Ser Leu Asp Thr Gln Lys Ala Thr Cys His Leu Gln Gln
225                 230                 235                 240
Val Thr Asp Leu Pro Trp Thr Ser Val Ser Ser Pro Val Glu Arg Glu
                245                 250                 255
Ile Leu Tyr His Thr Val Ala Arg Thr Lys Ile Ser Asp Asp Asp Asp
            260                 265                 270
Glu His Thr Leu
        275
```